United States Patent
Ohno et al.

(10) Patent No.: US 7,162,292 B2
(45) Date of Patent: Jan. 9, 2007

(54) BEAM SCANNING PROBE SYSTEM FOR SURGERY

(75) Inventors: Wataru Ohno, Hachioji (JP); Masaaki Ueda, Sagamihara (JP); Masahiko Kinukawa, Sagamihara (JP)

(73) Assignee: Olympus Corporation, Tokyo (JP)

( * ) Notice: Subject to any disclaimer, the term of this patent is extended or adjusted under 35 U.S.C. 154(b) by 441 days.

(21) Appl. No.: 10/146,832

(22) Filed: May 16, 2002

(65) Prior Publication Data

US 2002/0173783 A1 Nov. 21, 2002

(30) Foreign Application Priority Data

May 21, 2001 (JP) ............................. 2001-151090
Oct. 10, 2001 (JP) ............................. 2001-313015

(51) Int. Cl.
*A61B 5/05* (2006.01)

(52) U.S. Cl. ...................... 600/407; 600/410; 600/414; 600/415; 600/417; 600/425; 600/426; 600/429; 600/441; 600/443; 600/444; 600/445; 600/447; 600/449; 600/473; 600/476; 348/45; 358/400; 358/443

(58) Field of Classification Search ................ 600/407, 600/425, 426, 429, 443–5, 414, 417, 441, 600/447, 449, 410, 415, 473, 476; 606/2, 606/4, 6, 13–17; 348/45; 358/400, 443
See application file for complete search history.

(56) References Cited

U.S. PATENT DOCUMENTS

| | | | |
|---|---|---|---|
| 4,671,292 A * | 6/1987 | Matzuk ...................... 600/445 |
| 5,086,401 A | 2/1992 | Glassman et al. |
| 5,109,276 A * | 4/1992 | Nudelman et al. ............ 348/47 |
| 5,200,838 A * | 4/1993 | Nudelman et al. .......... 358/443 |
| 5,409,483 A * | 4/1995 | Campbell et al. ............. 606/15 |
| 5,471,988 A * | 12/1995 | Fujio et al. ................. 600/439 |
| 6,004,314 A | 12/1999 | Wei et al. |
| 6,006,126 A * | 12/1999 | Cosman ...................... 600/426 |
| 6,048,349 A | 4/2000 | Winston et al. |
| 6,081,336 A | 6/2000 | Messner et al. |
| 6,290,648 B1 * | 9/2001 | Kamiyama .................. 600/443 |
| 2002/0025082 A1* | 2/2002 | Kaushikkar et al. ........ 382/294 |
| 2002/0190212 A1* | 12/2002 | Boas et al. .............. 250/341.1 |
| 2004/0039378 A1* | 2/2004 | Lin ............................... 606/6 |

FOREIGN PATENT DOCUMENTS

| | | |
|---|---|---|
| JP | 6-154228 | 6/1994 |
| JP | 2000-121961 | 4/2000 |
| JP | 2000-126115 | 5/2000 |
| JP | 2000-171718 | 6/2000 |

\* cited by examiner

*Primary Examiner*—Brian L. Casler
*Assistant Examiner*—Baisakhi Roy
(74) *Attorney, Agent, or Firm*—Scully, Scott, Murphy & Presser, P.C.

(57) ABSTRACT

With the beam scanning probe system for surgery, a pointer indicating the observation point of a beam scanning probe is superimposed upon an image of a lesion to be operated on in the head which is obtained via a TV camera or a surgery microscope, and the superimposed image information is registered as such in an image recording device. With the beam scanning probe system for surgery, information of a cytological picture is also registered in the image recording device. With the beam scanning probe system for surgery, the image recording device registers the two image information in a paired fashion. Through this arrangement, the beam scanning probe system for surgery can smoothly locate, for a given cytological picture, a site of a tumor to be treated from which the picture was obtained, which will ease the operation.

6 Claims, 19 Drawing Sheets

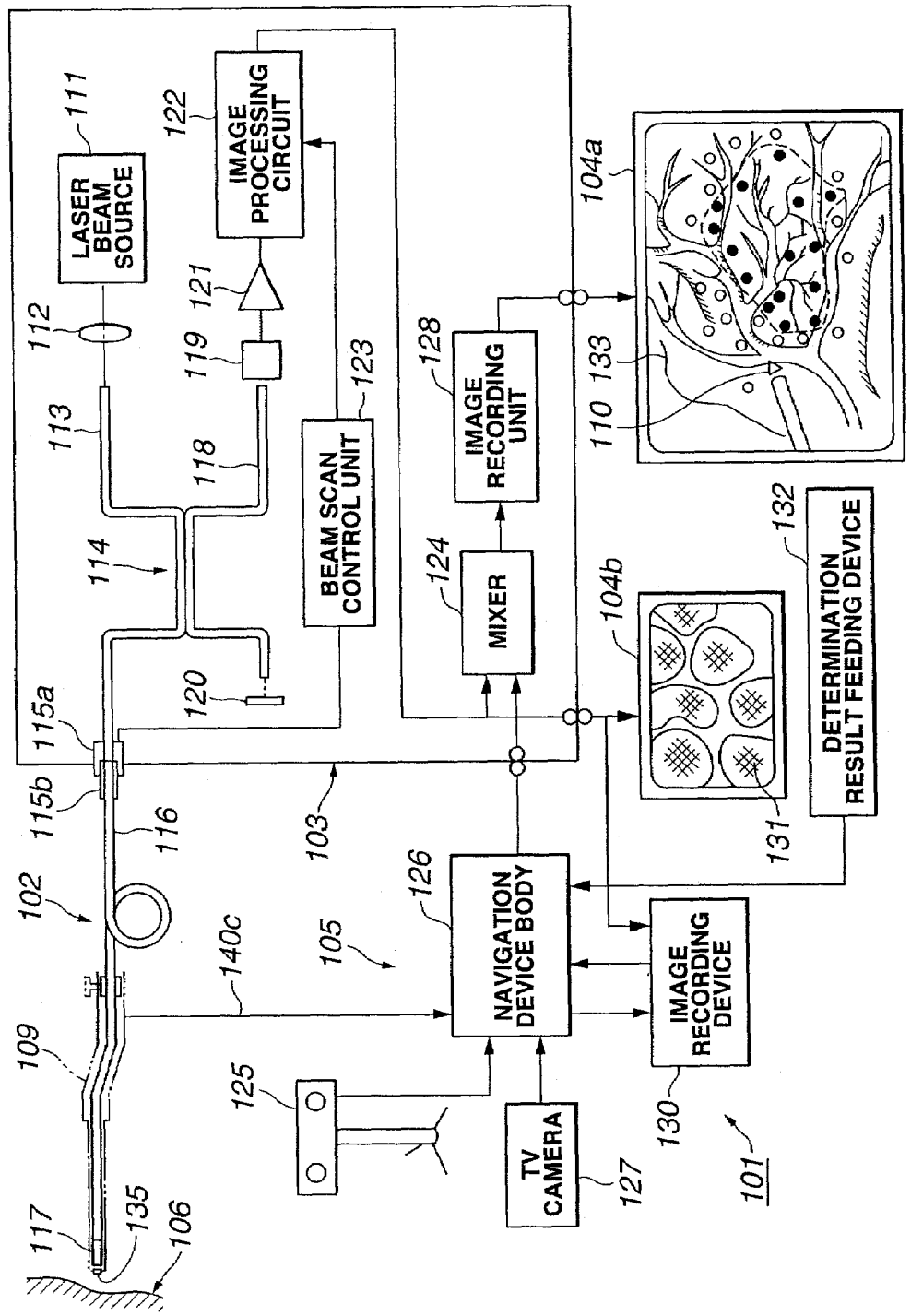

BEAM SCANNING PROBE SYSTEM FOR SURGERY

This application claims benefit of Japanese Applications No. 2001-151090 filed in Japan on May 21, 2001, and No. 2001-313015 filed in Japan on Oct. 10, 2001, the content of which are incorporated by this reference.

BACKGROUND OF THE INVENTION

1. Field of the Invention

The present invention relates to a beam scanning probe system for surgery for acquiring information about a tissue to be operated on using a beam scanning probe.

2. Description of the Related Art

Recently, beam scanning probe systems for surgery are widely used in brain surgery and other fields. The beam scanning probe system for surgery is for acquiring information about a tissue to be operated on using a confocal beam scanning probe.

Such a beam scanning probe includes, for example, those proposed by the present Applicants in Japanese Unexamined Patent Application Publication No. 2000-126115 (P2000-126115A), P2000-121961A and Japanese Unexamined Patent Application Publication No. 2000-171718 which are for conducting cytological diagnosis of a biological tissue by placing a probe at a confocal condition, scanning the test site kept at a focus, and gathering optical information from the site.

A similar beam scanning probe for surgery is proposed in the field of brain surgery which enables cytological diagnosis of a biological tissue under a microscope, like the one previously described by the present Applicants in Japanese Unexamined Patent Application Publication No. 6-154228.

Excision of a tumor in brain surgery requires previous pathological examination of many sites on and around the tumor to be excised. If the tumor develops in the parenchyma of the brain, the operator must determine how to approach it and how to excise it depending on its benign/malignant nature determined based on the pathological examination. Particularly, if operation is performed on a malignant tumor, it must be determined based on the pathological examination of the tumor performed during operation whether the entire tumor should be excised, or whether surgical invasion into the surrounding brain parenchyma should be kept minimal with certain parts of the tumor left intact, that is, how the boundary between the excised part and the intact part should be defined. In such a situation, if there are certain sites of the tumor whose pictures do not permit definite diagnosis, the operation should be interrupted until a pathological examiner makes a definite diagnosis, or should be completely withdrawn. In the latter case, a renewed surgery will be required.

Although methods for making cytological diagnosis using a conventional beam scanning probe system for surgery have been disclosed, the conventional system does not permit the operator to precisely define a lesion in the brain structure, even less to reproduce it on display, and moreover requires the presence of a pathological examiner on the site.

Further, if a conventional beam scanning probe system for surgery is used for cytological examination, the relation between a site of which diagnosis is made, and an image obtained therefrom, and the extent of a lesion on that site are separately treated from each other. On account of this, as long as the conventional beam scanning probe system is used for cytological examination, those separate data must be organized before a proper operation plan is established.

Incidentally, the beam scanning probe includes, for example, one described in U.S. Pat. No. 6,004,314 which examines tissues exposed to a laser beam, and determines the affected tissues.

The beam scanning probe also includes, for example, one described in U.S. Pat. No. 6,048,349 which is for introducing a treatment tool through the human body.

SUMMARY OF THE INVENTION

The beam scanning probe system for surgery according to this invention comprises an image acquiring means for acquiring an image of a site to be operated on (lesion hereinafter) in the head or the like; a beam scanning probe for acquiring optical image information of a specific site of the lesion; a detection means for detecting the position of the site relative to the observation position of the beam scanning probe; and a recording means for registering cytological picture information obtained via the beam scanning probe, and image information of the lesion upon which the position information of the beam scanning probe is superimposed in a paired fashion.

Alternatively, the beam scanning probe system for surgery of this invention comprises:

an image acquiring means for acquiring image information of a lesion of a test organ;

a monitor for displaying an image of the lesion based on the image information of the lesion;

a beam scanning probe for acquiring image information regarding the histology of a specific site of the lesion selected based on the image of the lesion;

a rigid sheath through which the beam scanning probe can be inserted to the tip, the rigid sheath being able to guide the beam scanning probe advanced to the tip to the specific site;

a marker provided to the rigid sheath which is apart from the tip of the rigid sheath by a predetermined distance;

a detector for detecting positional information of the marker in a three-dimensional space;

a superimposed image generating circuit for obtaining positional information of the beam scanning probe in the three-dimensional space based on the positional information of the marker in the three-dimensional space, for correlating the positional information of the beam scanning probe with the image information of the lesion in the three-dimensional space, and for obtaining superimposed image information consisting of the image information of the lesion upon which the positional information of the beam scanning probe is superimposed; and a memory for relating the histological image information and superimposed image information with the positional information of the beam scanning probe, and for storing the information as such.

BRIEF DESCRIPTION OF THE DRAWINGS

FIG. 11 shows the composition of a beam scanning probe system representing a third embodiment of this invention;

DETAILED DESCRIPTION OF THE PREFERRED EMBODIMENTS

Preferred embodiments of this invention will be described below with reference to the accompanying drawings.

(First Embodiment)

Figure 1:
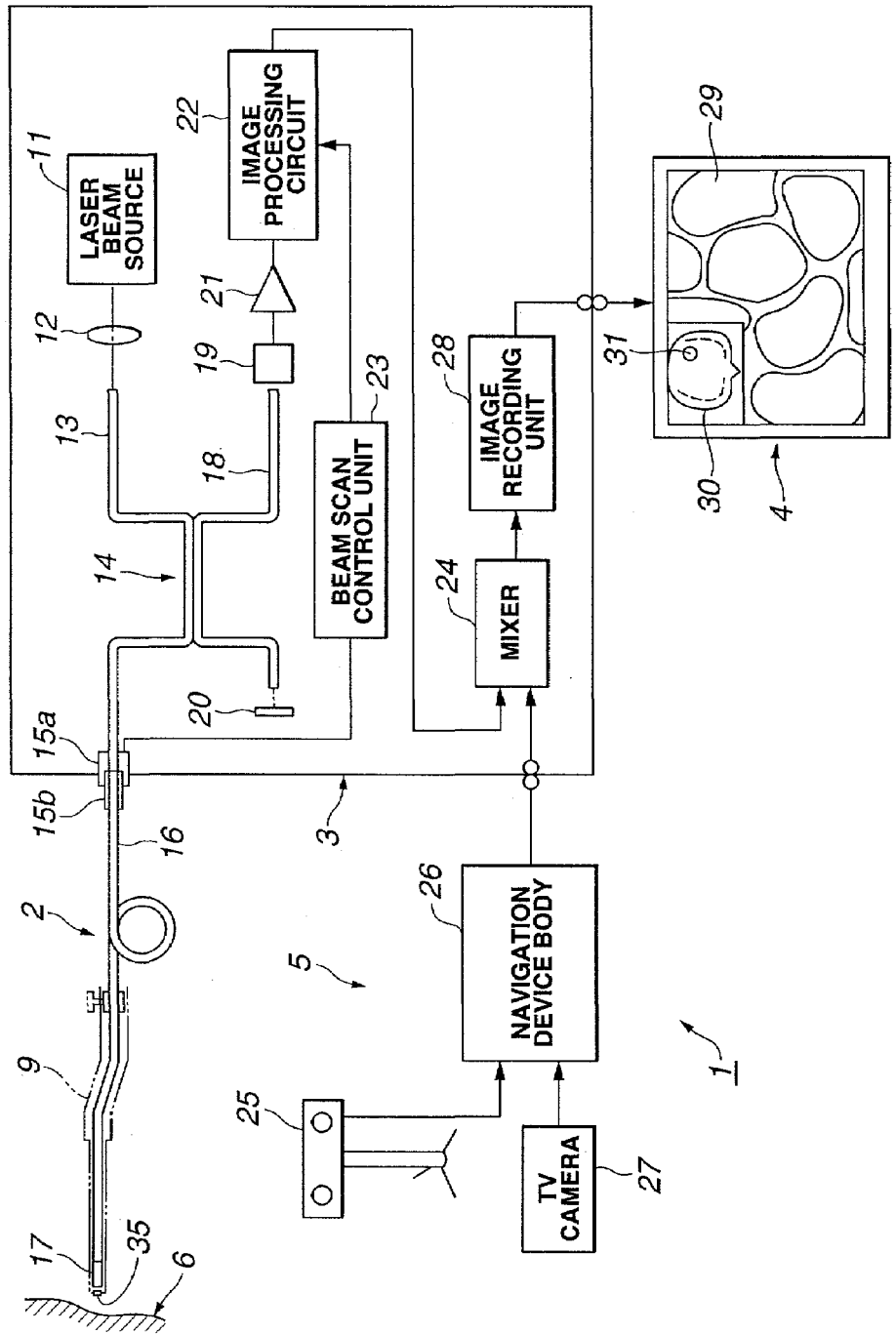
FIG. 1 shows the composition of a beam scanning probe system representing a first embodiment.
Figure 2:
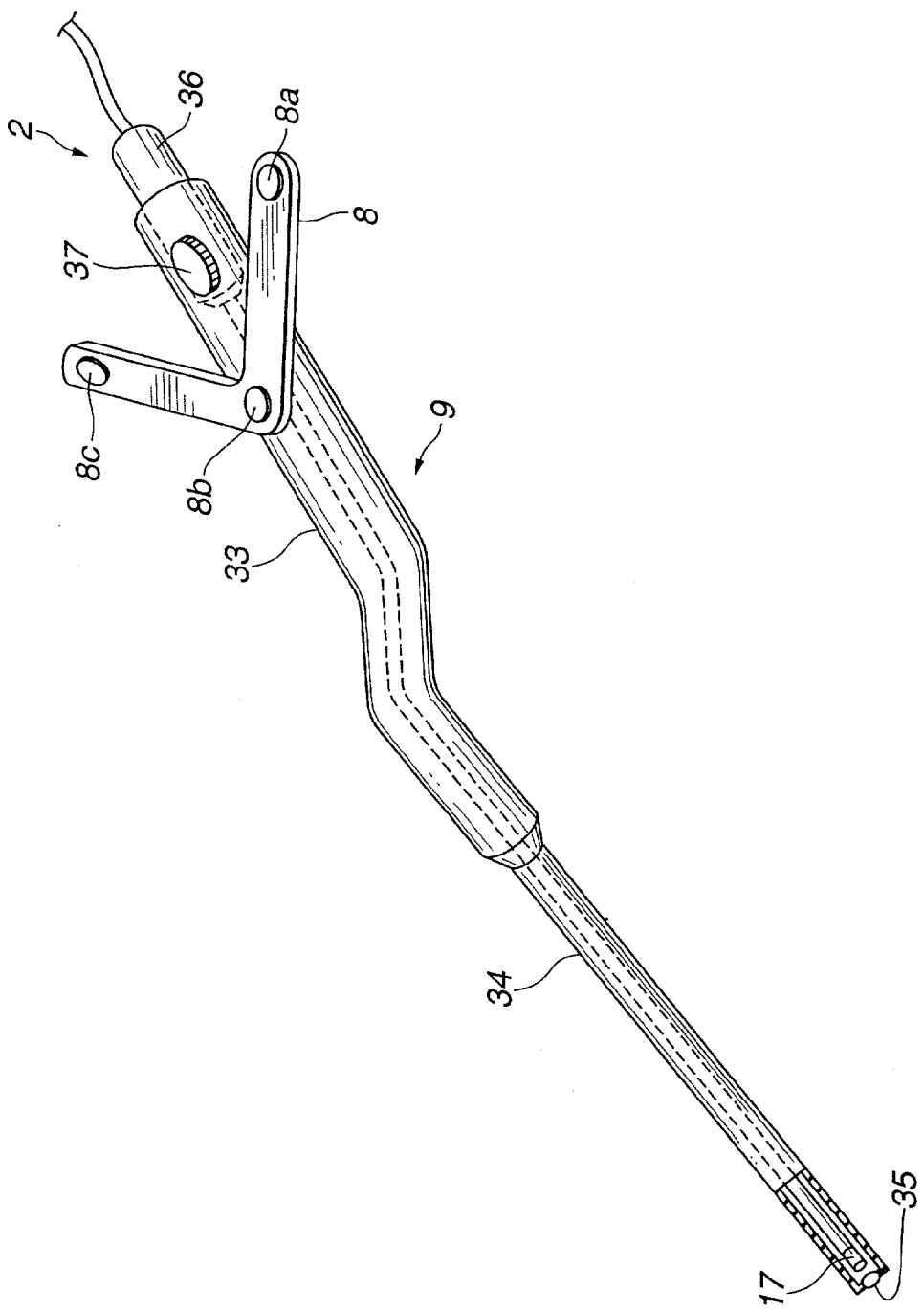
FIG. 2 is a perspective view of a rigid sheath into which a beam scanning probe is inserted.
Figure 3:
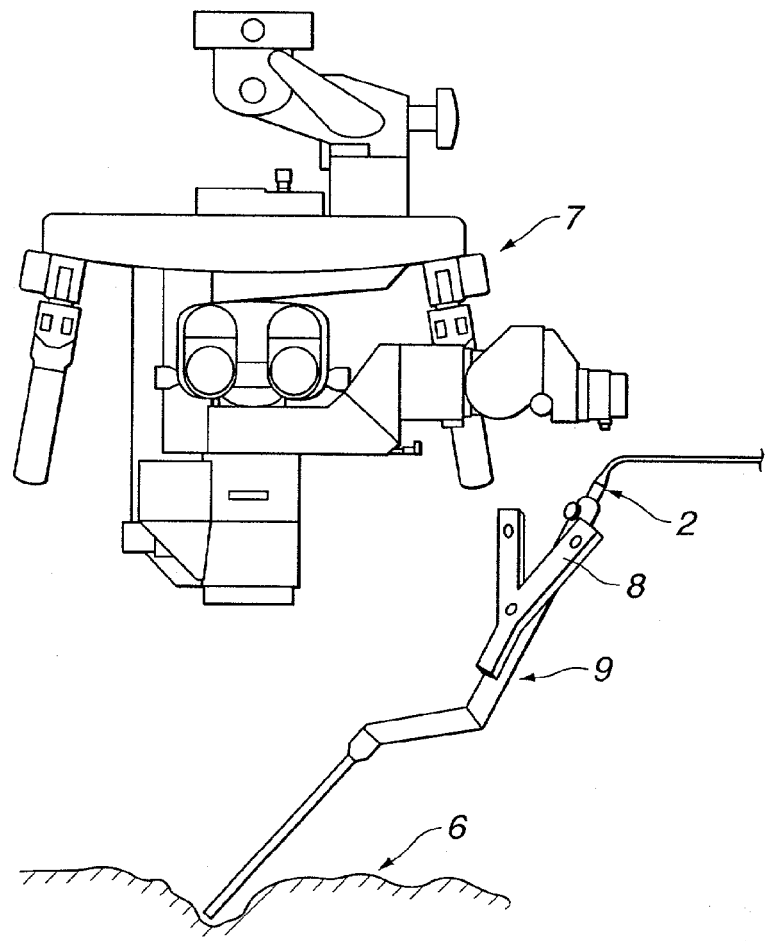
FIG. 3 shows how a confocal image of a lesion is obtained via the beam scanning probe under the observation via a surgery microscope.
Figure 4:
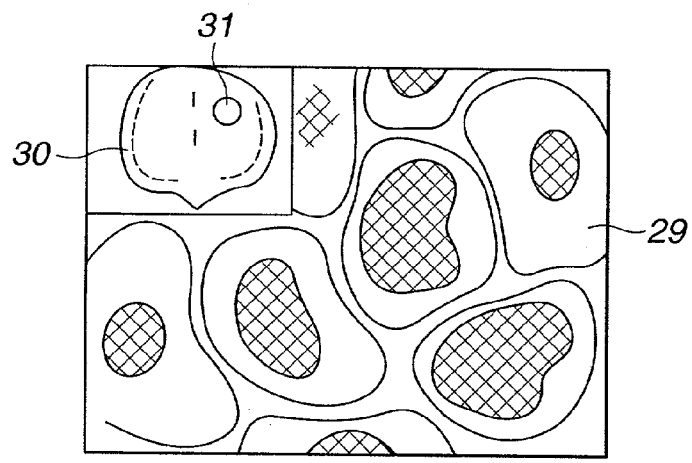
FIG. 4 shows images displayed on a monitor.
Figure 5:
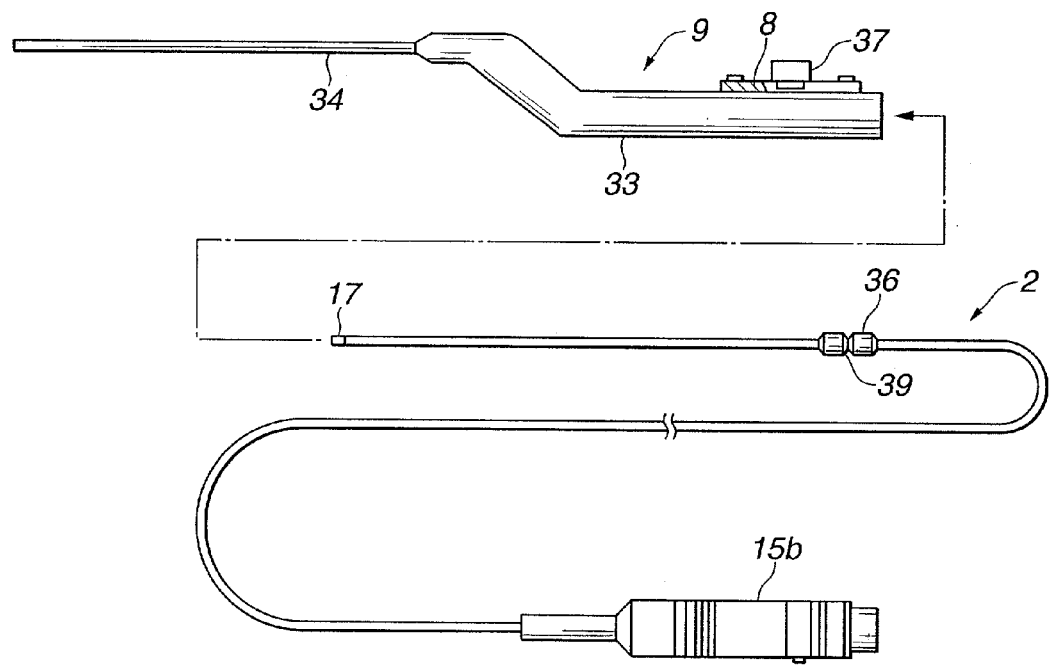
FIG. 5 shows the rigid sheath, and the beam scanning probe which is detachably inserted through the sheath.
Figure 6:
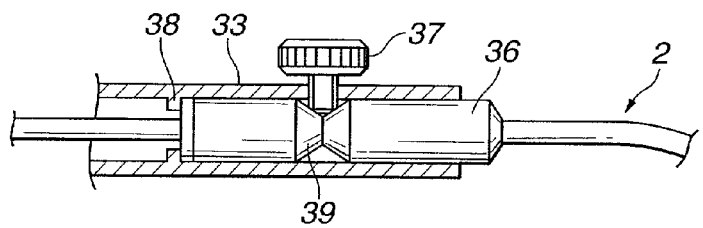
FIG. 6 shows a cross-section of a part close to a fixing section when the beam scanning probe is properly placed with respect to the rigid sheath.

FIGS. 1 to 6 relate to a first embodiment of this invention: FIG. 1 shows the composition of a beam scanning probe system representing a first embodiment; FIG. 2 is a perspective view of a rigid sheath into which a beam scanning probe is inserted; FIG. 3 shows how a confocal image of a lesion is obtained by the beam scanning probe under the observation via a surgery microscope; FIG. 4 shows images displayed on a monitor; FIG. 5 shows the rigid sheath, and the beam scanning probe which is detachably inserted through the sheath; and FIG. 6 shows a cross-section of a part close to a fixing portion when the beam scanning probe is properly placed with respect to the rigid sheath.

As shown in FIG. 1, the beam scanning probe system for surgery 1 representing the first embodiment of this invention comprises a confocal beam scanning probe 2 (to be referred to simply as beam scanning probe hereinafter); an observation system 3 to which the proximal end of the beam scanning probe 2 can be detachably connected, and which provides a laser beam to the beam scanning probe 2, and processes image information conveyed by light reflected by a test organ, or more specifically by a cranial lesion; a monitor 4 for displaying a confocal image derived from the information upon input of image signals output from the observation system 3; and a navigation device 5 for detecting the observation position of the beam scanning probe 2.

The beam scanning probe system for surgery 1 further comprises a surgery microscope 7 for enlarging the view of a site in the lesion 6 of the head to be operated on (see FIG. 3). According to this embodiment, the beam scanning probe 2 is configured such that it is inserted into a rigid sheath 9 which is equipped with a light emitting portion 8 for helping the positional detection as shown in FIG. 2.

The observation system 3 incorporates a laser beam source 11. A laser beam emanating from the laser beam source 11 is fed via a converging lens 12 into a single mode fiber 13.

The laser beam passing through the single mode fiber 13 is conveyed via a coupler section 14 inserted midway and a connector 15b jointed to a connector socket 15a to another single mode fiber 16 running within the beam scanning probe 2.

The single mode fiber 16 is connected, at the distal end of the probe, to a beam scanning head 17 which scans the beam. A laser beam (delivered via a converging lens 35 attached to the distal end of the rigid sheath 9) is scanned by the beam scanning head 17 over a two-dimensional space around a lesion 6 of a test organ.

Light reflected by the lesion 6 impinges (via the converging lens 35 and the beam scanning head 17) on the distal end of the single mode fiber 16, and passes through the same path in the reverse direction towards the coupler section 14. Part of the light guided to the coupler section 14 is diverged into a third single mode fiber 18.

The distal end of the single mode fiber 16 has a sufficiently small surface area. A laser beam emanating from the distal end of the single mode fiber 16 is converged via an optical system including the converging lens 35 onto the lesion 6. In this process, the laser beam emanating from the distal end of the single mode fiber 16 is focused into a spot at a position which allows reflected light therefrom to take a confocal relation to the distal end of the single mode fiber 16 via the intervening optical system such as the converging lens 35.

Further, out of light reflected by the lesion 6 and converged by the optical system including the converging lens 35, only the component that has been reflected from the focusing position is allowed to enter the distal end of the single mode fiber 16. Briefly, the observation system 3 is configured such that it allows only light (also called returning light) reflected from a confocal position to enter the distal end of the single mode fiber 16.

The returning light is transmitted via the proximal (rear) end of the single mode fiber 18 to an optical sensor 19. Within the observation system 3, a damper 20 is placed opposite to the distal end of the single mode fiber 18. The damper 20 is for attenuating light emanating from the distal end of the single mode fiber 18 (that is, the damper forms a blind end where no reflection of light occurs).

A detection signal which is produced as a result of photoelectric conversion at the photo sensor 19 is amplified by an amplifier 21 to be fed to an image processing circuit 22. The image processing circuit 22 is for reconstructing an image from detection signals using scan control signals delivered by a beam scan control circuit 23 which controls the beam scanning head 17. The image signals formed by the image processing circuit 22 are fed to a mixer 24.

The navigation device 5 includes a digitizer 25 for positional detection. The digitizer 25 for positional detection detects, for example, infra-red rays emitted by a light emitting portion 8, and delivers a position signal obtained from the rays to the navigation device body 26.

The navigation device body 26 also receives signals carrying, for example, an image of a cranial lesion (including the lesion 6 to be operated) delivered by a surgery microscope 7, or by a TV camera 27 placed close to the microscope both of which serve as an image acquiring means.

Each of the image acquiring means is equipped with a mechanism similar to the light emitting portion 8. The position of an image acquired by the image acquiring means in a three-dimensional space is determined based on the detection by the digitizer 25 of the rays emitted by the light emitting portion. The position of the image in a three-dimensional space is fed together with the image information to the navigation device body 26.

The navigation device body 26 delivers the image information regarding the head and the three-dimensional position information to a mixer 24. The navigation device body 26 further determines the position of an image of the lesion in the three-dimensional space provided by the beam scanning head 17 which is apart by a predetermined distance from the light emitting portion 8, based on the position information of the light emitting portion 8 provided by the digitizer 25. The navigation device body 26 makes a processing necessary for obtaining a navigation image, that is, processes relevant signals so as to produce an image signal in which the point of observation taken by the beam scanning head 17 is superimposed over the image of the lesion obtained by the image acquiring means.

To put it specifically, the navigation device body 26 generates an image signal representing a pointer which indicates the observation point of the beam scanning head 17 over an image of the head (or of the cranial lesion). Then, the navigation device body 26 delivers the image signal representing a pointer to the mixer 24.

The navigation device body 26 detects the position of the beam scanning head 17 and the direction of its optical axis with respect to the light emitting portion 8 shown in FIG. 2, which is apart from the former by a predetermined distance and in a predetermined direction, by determining the positions of a plurality of light emitting elements 8a–8c contained in the light emitting portion 8. Then, the navigation device body 26 takes the position of the lesion along the optical axis thus detected as the point of observation.

A confocally scanned image obtained by the beam scanning probe 2 and fed to the mixer 24, and a navigation image from the navigation device 5 are mixed such that the corresponding positions of the two images in the three-dimensional space coincide with each other to give a conjugated image which is fed to an image recording device 28. The two images are recorded in a paired fashion, and fed to a monitor 4.

The image acquiring means may comprise a CT/MRI system, in addition to the surgery microscope 7. The CT/MRI system may be used for obtaining an image for diagnosis, prior to surgery. Namely, the image obtained by the CT/MRI system is presented such that its position in a three-dimensional space is coincident with the position taken by the beam scanning probe 17 during observation in the same three-dimensional space. Moreover, if the position of the beam scanning head 17 is superimposed on the image obtained by CT/MRI, it will be possible to utilize the resulting image similarly to a navigation image.

General navigation systems used in the medical field are described in U.S. Pat. Nos. 6,006,126 and 5,086,401 which will be incorporated herein by this reference.

The display of the monitor 4 will give two kinds of images: a cytological picture 29 i.e., a confocally scanned image together with a diagnostic picture taken prior to surgery as shown in FIG. 4, or with a navigation image 30. The navigation image 30 includes a pointer 31 representing the observation point of the beam scanning head 17.

FIG. 2 shows the overview illustrating the shape of the beam scanning probe 2 and the bayonet type rigid sheath 9.

The hollow, bayonet type rigid sheath 9 comprises a rigid handle portion 33 including at least two bends, and a constricted sheath portion 34 (sheath insertion segment) which is obtained by constricting the distal end of the handle portion 33 to give a rigid tube having a smaller diameter.

The rigid sheath 9 receives the insertion of the beam scanning probe 2 from the proximal (rear) end of its handle portion 33. The beam scanning probe 2 is properly positioned with respect to the rigid sheath 9 such that its distal end is close and opposite to the converging lens 35 attached to the distal end of the constricted sheath portion 34, and then the joining portion 36 of the beam scanning probe 2 is detachably fixed by a fixation pin 37.

The rigid sheath 9 has on a rear part of the handle portion 33 the light emitting portion 8 responsible for positional detection by position digitizer 25. The light emitting portion 8 carries a number of light emitting elements 8a–8c which emit infra-red rays.

FIG. 5 shows the bayonet type rigid sheath 9 and the beam scanning probe 2 separated from each other.

With the beam scanning probe 2, the joining portion 36 is placed by a standardized distance apart from the beam scanning head 17 attached to the distal end of the beam scanning probe 2. To allow the joining portion 36 to take a proper position, the rigid sheath 9 has positioning projections 38 in the interior of the proximal end of the handle portion 33 and the fixation pin 37 with a screw end as shown in FIG. 6.

The rigid sheath 9 determines the beam scanning probe 2 to be properly positioned when a larger bore end of the joining portion 36 of the beam scanning probe 2 strikes against the positioning projections 38. Then, the fixation pin 37 is screwed in until its screw end fits to a V notch 39 formed on the joining portion 36 and the beam scanning probe 2 is properly positioned with respect to the rigid sheath 9.

With the beam scanning probe 2, a connector 15b at its rear end is detachably connected to a connector socket 15a of the observation system as shown in FIG. 1. The connector 15b also includes connector pins (not illustrated here) connected to signal lines leading to the beam scanning head 17. The beam scanning probe 2 is connected via the connector socket 15a to the beam scan control circuit 23.

The embodiment configured as above is characterized by registering into the image recording device 28 a pre-surgery diagnostic image of the part to be operated on, such as cranial lesion, combined with positional information regarding the point of observation subsequently taken by the beam scanning probe 2 for scrutiny, and a cytological image 29 actually obtained by the beam scanning probe 2 in a paired fashion.

The operation of the embodiment configured as above will be described below.

The operator inserts the beam scanning probe 2 into the bayonet type rigid sheath 9 as shown in FIG. 5, until the proximal end of the joining portion 36 of the beam scanning portion 2 strikes against the positioning projections 38 provided on the interior of the rigid sheath 9. Then, the operator screws in the fixation pin 37 until the pin's end strikes against the slopes of the V notch 39 formed on the joining portion 36, and thus ensures that the beam scanning probe 2 is properly positioned with respect to the rigid sheath.

Then, the operator connects the connector 15b of the beam scanning probe 2 to the observation system 3 as shown in FIG. 1. The operator also connects the navigation device 5 to the observation system 3 as shown in FIG. 1. The beam scanning head 17 of the beam scanning probe 2 thus properly placed in the rigid sheath 9 is guided to a lesion 6 under the monitoring via the surgery microscope 7.

Then, an image of the cranial lesion before surgery obtained by the TV camera 7 is presented on the monitor 4 as a navigation image 30. A pointer 31 is also presented on the navigation image 30. The pointer 31 indicates the point of observation towards the lesion (or a desired spot on the lesion 6) taken by the beam scanning probe 2 of the beam scanning head 17 for microscopic observation of that spot.

As shown in FIG. 1, confocal optical signals obtained by the beam scanning head 17 of the beam scanning probe 2 from the observation point is converted by the image processing circuit 22 into video signals carrying a confocally scanned image, or in this case a cytological picture 29. The video signal is fed to the mixer 24.

The two image signals are combined by the mixer 24 and transmitted to the image recording device 28 as well as to the monitor 4. Thus, the monitor 4 displays the cytological picture 29 as well as the navigation image 30 as shown in FIG. 4.

Because the distal end of the beam scanning probe 2 is properly fixed with respect to the rigid sheath 9 having thereon the light emitting portion 8 enabling positional detection, the operator, during operation, can handle the beam scanning probe 2 as easily as with conventional treatment forceps, and select a site for diagnosis (observation) under microscopic monitoring while keeping the operator's sight from being disturbed by the presence of the surgery microscope 7.

As discussed above, according to this embodiment, image information is recorded such that a pre-surgery diagnostic image of a cranial lesion, and a microscopic cytological picture 29 obtained via the beam scanning probe 2 from a position marked on the diagnostic image can be displayed in combination. Because of this, according to this embodiment, the pathologist-operator can smoothly make a pathological diagnosis based on the paired image information.

Namely, the pathologist-operator can not only determine whether a given abnormality is a tumor or not based on its cytological picture 29, but also exactly locate the abnormality based on the pointer 31 indicating the location from which the cytological picture 29 has been obtained. Accordingly, by repeating the same observation on plural lesions 6 on and around the abnormality, the pathologist-operator can smoothly make a diagnosis on its pathological nature including its extent.

Based on the diagnosis result, the pathologist-operator can smoothly determine how the tumor should be excised, and what post-surgery treatment should be taken.

Thus, this embodiment will ensure following advantages.

The embodiment will allow the pathologist-operator to smoothly make a pathological diagnosis and to perform an operation. This embodiment will reduce time required for operation which will contribute for relieving the operator and the patient of strain and pain.

To put it specifically, according to this embodiment, a cytological picture 29 and an image including the diagnosis site from which the picture has been taken are combined for display/recording, and thus the operator can easily recognize the correlation of the microscopic cytological picture with its actually viewed site. Further, according to this embodiment, the operator can identify a cytological picture currently displayed in its viewed site on a pre-surgery diagnosis image. Thus, the operator can easily identify the location of the cytologically viewed site which would be important, if the site includes a tumor, for determining the malignancy of the tumor.

According to this embodiment, the operator can easily obtain, even during operation, a cytological picture of a desired site by referring to a pointer 31 and to information given by a cytological picture 29 obtained via the beam scanning probe 2, and thus easily approach the site to be operated on. Therefore, according to this invention, the operator can smoothly make an operation being relieved of complications which would otherwise intervene. This embodiment will be also advantageous to the patient because it will shorten the time required for operation.

According to this invention, if it is required to adjust the length of the rigid sheath 9 which will be inserted into a lesion, this will be met by preparing a number of rigid sheaths 9 having different tip lengths.

If it is required to prepare a rigid sheath 9 longer than the one described with regard to this embodiment, it is only necessary to displace the fixing pin 37 towards the tip, and to elongate the constricted portion of the rigid sheath 9 by the same displacement distance. According to this embodiment, a variety of bayonet type rigid sheaths 9 in which the position of the fixing pin 37 varies may be made available so that a rigid sheath having an appropriate insertion length for a given lesion may be chosen.

Further, because the beam scanning probe 2 is a soft probe, it is easy to prepare a number of probes different in shape and length as with the rigid sheath 9, so that the operator can choose an appropriate one for a given operation.

(Second Embodiment)

Next, a second embodiment of this invention will be described with reference to FIGS. 7 to 10B.

Figure 7:
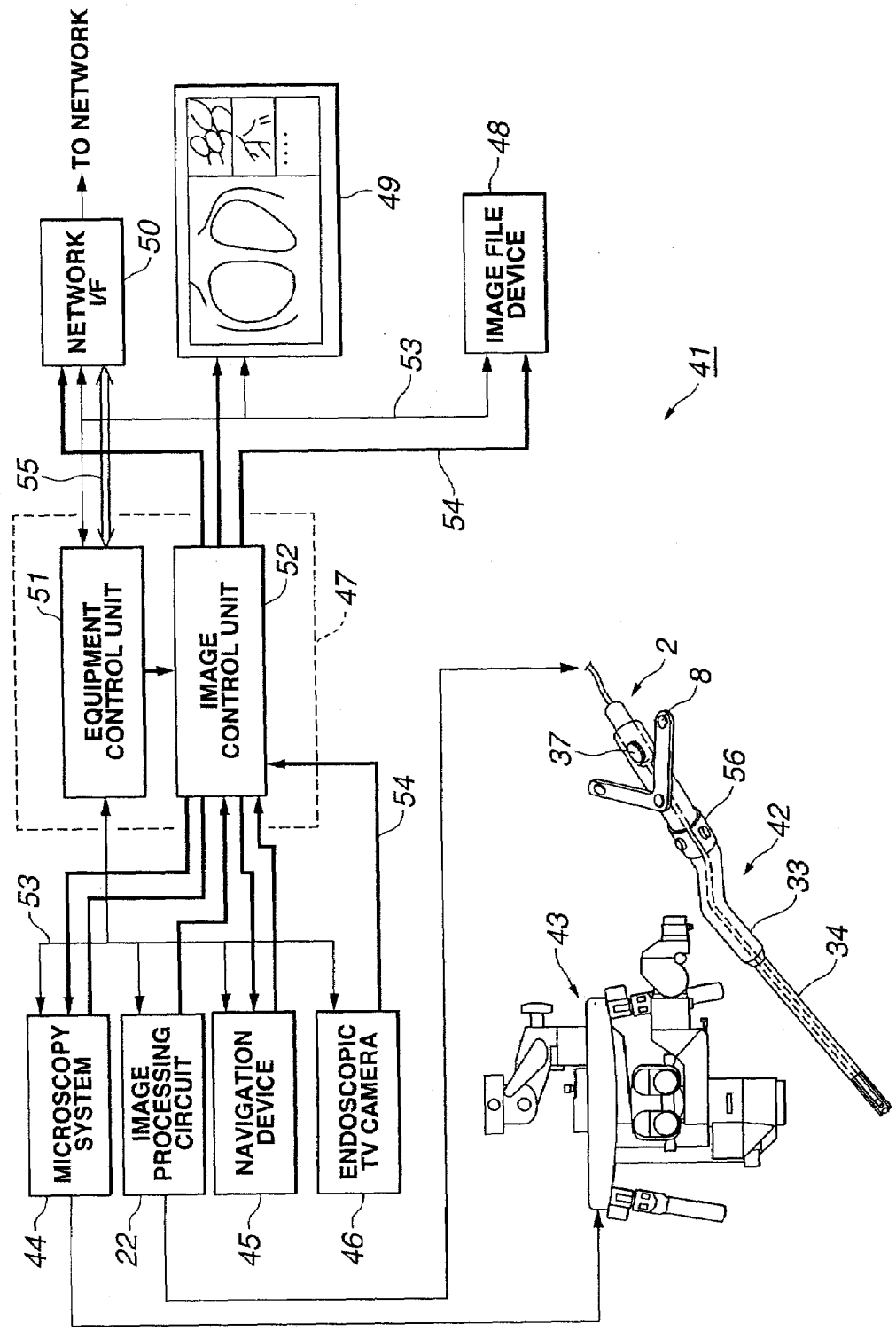
FIG. 7 shows the composition of a beam scanning probe system representing a second embodiment of this invention.
Figure 8:
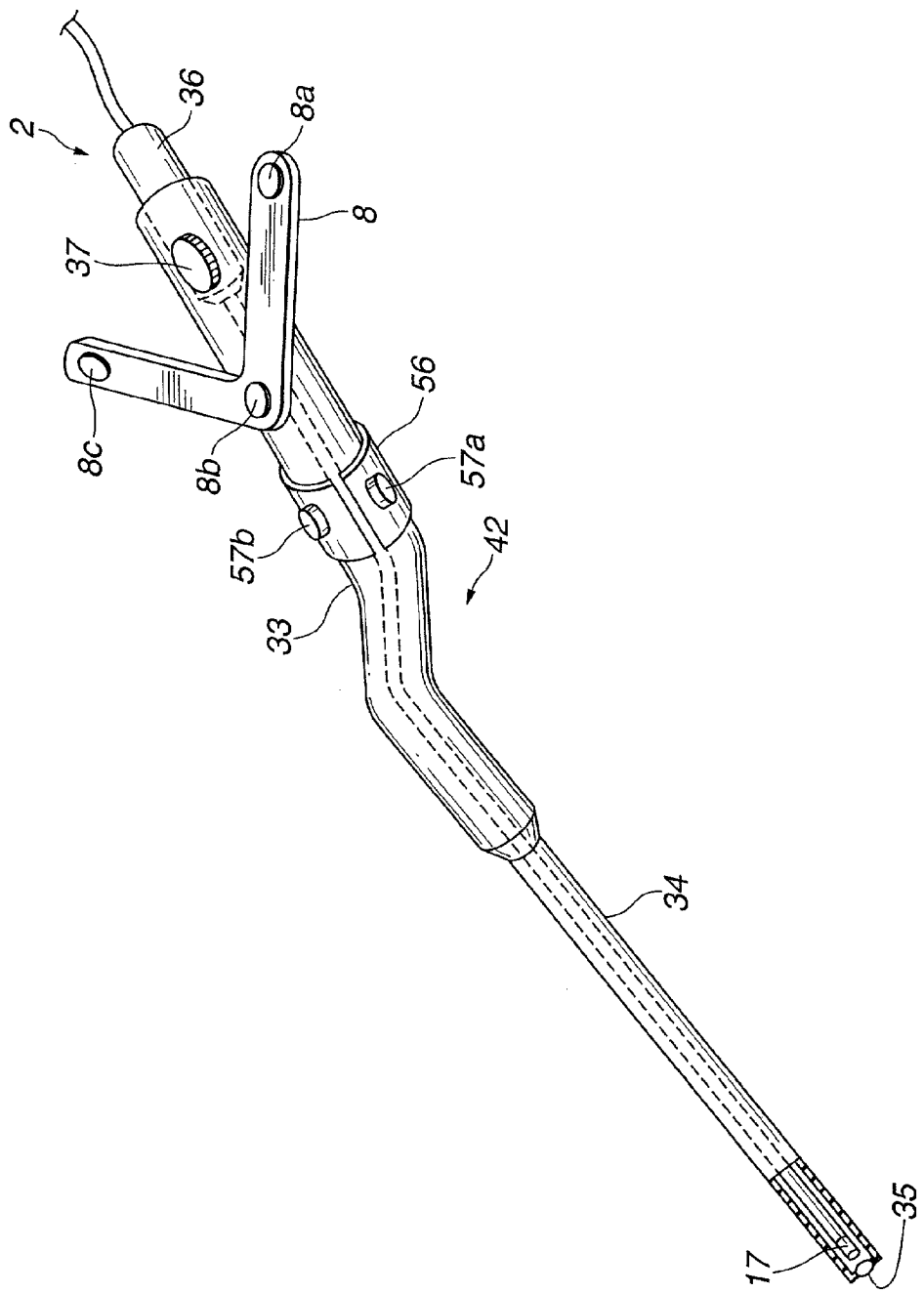
FIG. 8 is a perspective view of a rigid sheath into which a beam scanning probe is inserted.
Figure 9:
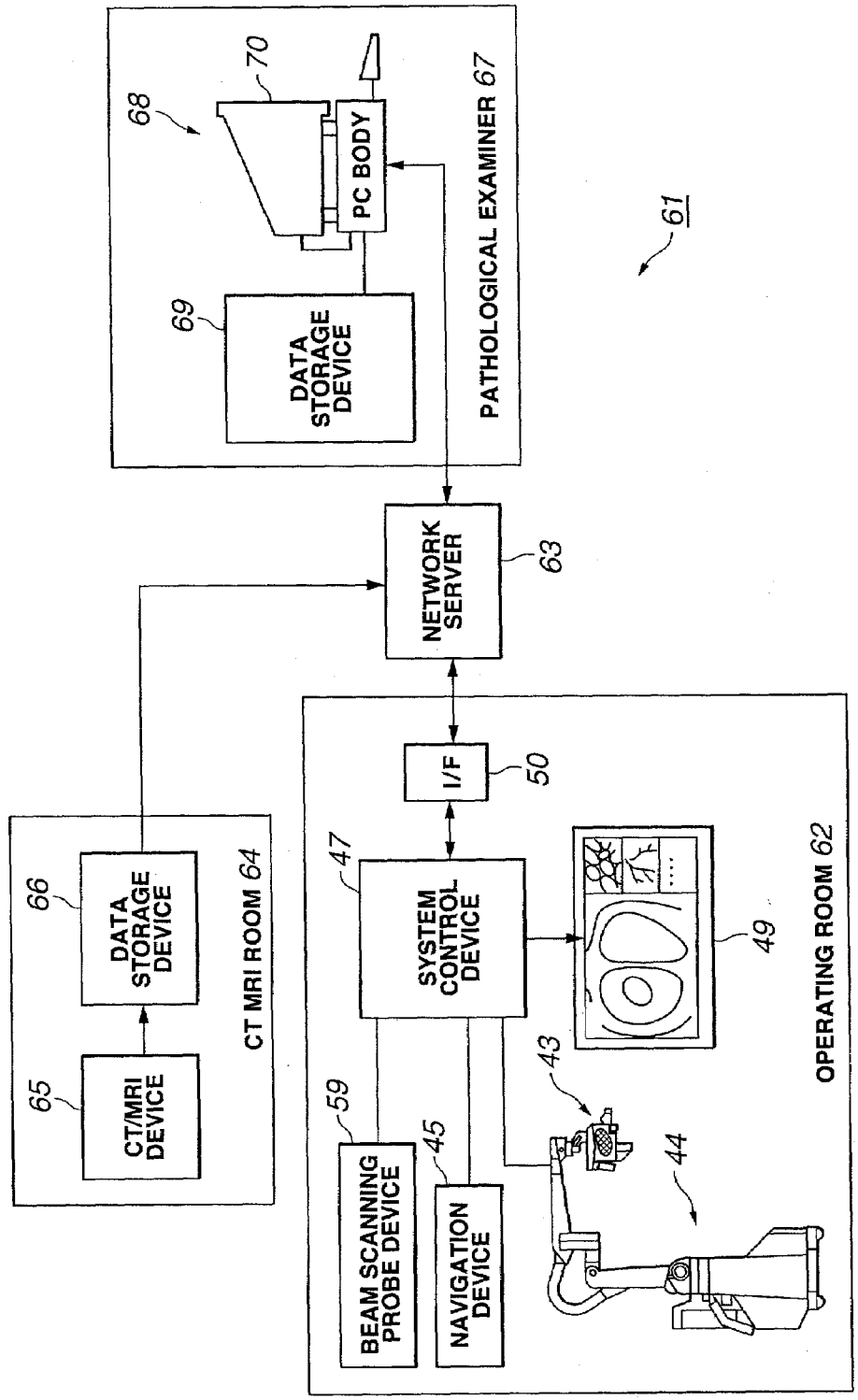
FIG. 9 shows the composition of the beam scanning probe system used in a hospital, or used between hospitals.
Figure 10A:
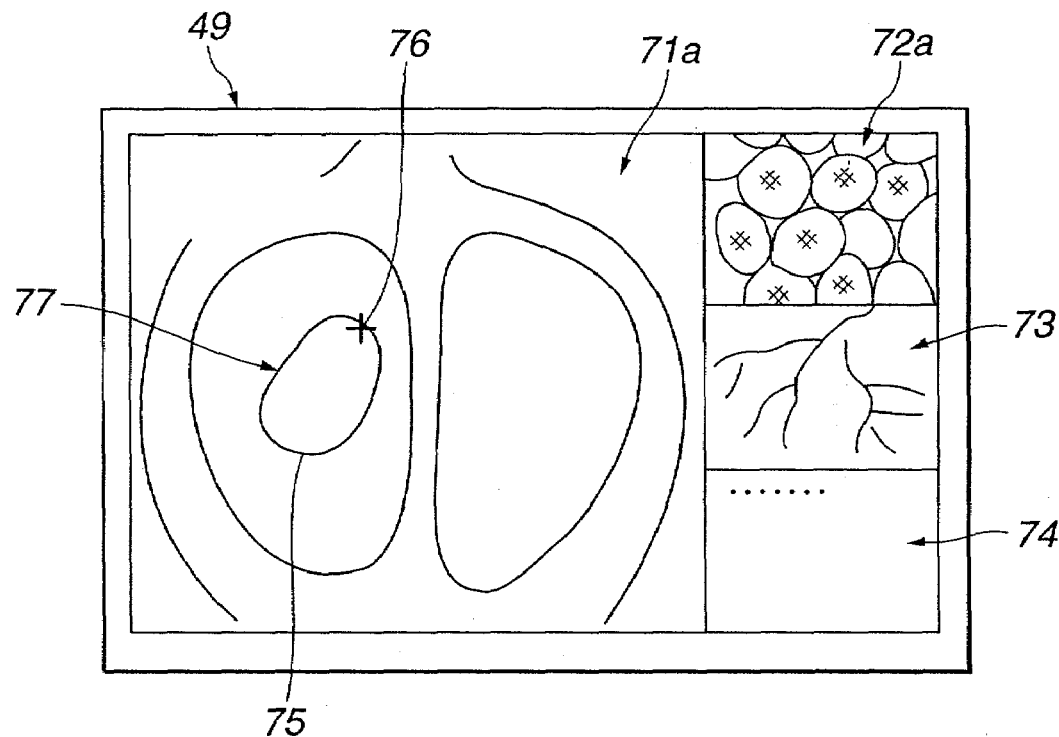
FIG. 10A shows exemplary images displayed on a TV monitor of an operating room.
Figure 10B:
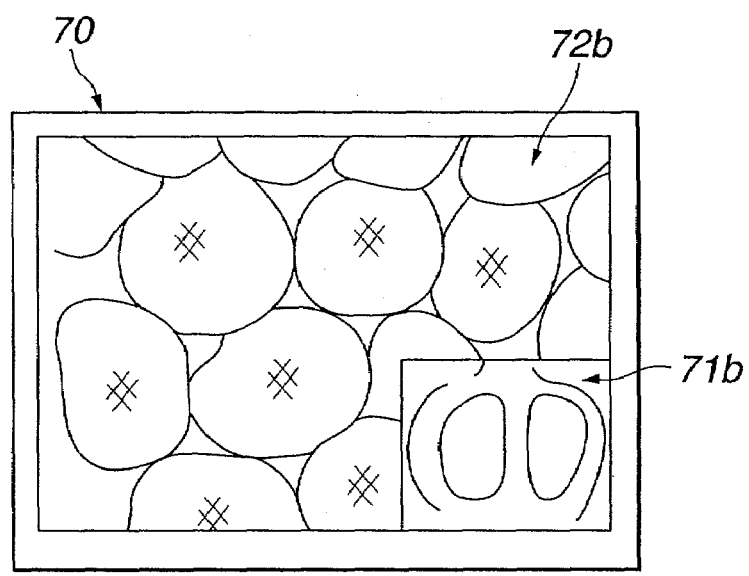
FIG. 10B shows exemplary images displayed on a monitor of a pathological examiner.

FIG. 7 shows the composition of a beam scanning probe system for surgery representing the second embodiment of this invention; FIG. 8 shows an appearance of a rigid sheath receiving the insertion of a beam scanning probe; FIG. 9 shows the composition of a beam scanning probe system for surgery utilized in a hospital or between hospitals; FIG. 10A shows an exemplary display of images presented on a monitor in an operating room; and FIG. 10B shows an exemplary display of images on a monitor used by a pathological examiner.

With the beam scanning probe system 41 shown in FIG. 7, the rigid sheath 42 receiving the insertion of the beam scanning probe 2, and a surgery microscope 43 are connected via an image processing circuit 22 and a microscopy system 44 respectively to a system control device 47. A navigation device 45 and an endoscopic TV camera 46 are connected to the system control device 47. The beam scanning probe system for surgery 41 comprises an image file device 48 which is connected to the system control device 47, and which combines an image obtained via the navigation device 45 and an image obtained via the beam scanning probe 2 in a paired fashion as in the first embodiment for registration, a TV monitor 49, and a network interface 50 connected to a network.

The system control device 47 controls equipment connected thereto including the microscopy system 44 and others (systems and devices), and comprises an equipment control unit 51 responsible for transmitting image data via the network interface 50 to external machines, and for receiving image data from external machines, and an image control unit 52 responsible for controlling image signals handled by equipment connected thereto.

The equipment control unit 51 is connected via a local communication line 53 such as RS232C to the microscopy system 44, the image processing circuit 22, the navigation device 45, an endscopic TV camera 46, the image file device 48, the TV monitor 49 and the network interface 50.

The image control unit 52 is connected via an image communication line 54 to the microscopy system 44, image processing circuit 22, navigation device 45, endscopic TV camera 46, image file device 48, TV monitor 49 and network interface 50. The image control unit 52 controls such that image inputs from the beam scanning probe 2 and from the endscopic TV camera 46 are output to the image file device 48 and to the TV monitor 49.

The equipment control unit 51 is connected via a data line 55 to the network interface 50. The equipment control unit 51 transmits image signal data, voice data, computer data, etc., via the network interface 50 through the data line 55, and receives signals from external sources.

According to this embodiment, the beam scanning probe 2 is also inserted into the rigid sheath 42 as shown in FIG. 8.

The rigid sheath 42 may be obtained by adding a remote switch holder 56, for example, to the handle portion 33 of the rigid sheath 9 shown in FIG. 2. The remote switch holder 56 carries at least two remote switches 57a and 57b.

Signals produced by activating the remote switches 57a and 57b are transmitted via a remote signal line not shown here to the equipment control unit 51.

If the operator catches a desired site by operating the beam scanning probe 2, he switches ON the remote switch 57a. Then, the system control device 47 works such that the site chosen by the operator is indicated with a marker on a navigation image currently on display.

Then, if the operator switches ON the remote switch 57b, the system control device 47 works such that the cytological picture of the site chosen by him will be recorded. The system control device 47 is also configured such that the cytological picture thus recorded can be transmitted via a network to an external machine, more specifically, to a personal computer 68 in front of a pathological examiner 67 as will be described later.

The process introduced for converting signals produced by the beam scanning probe 2 of the beam scanning head 17 into an image is the same as in the first embodiment. The other features are also the same with those of the first embodiment.

FIG. 9 shows an exemplary composition of a beam scanning probe system for surgery 61 utilized in a hospital or between hospitals.

In an operating room 62, a surgery microscopy system 44, a beam scanning probe device 59 (including a beam scanning probe 2 inserted into a rigid sheath 42, and an image processing circuit 22), a navigation device 45, a TV monitor 49 and others as shown in FIG. 7 are connected to a system control device 47. The system control device 47 is connected via a network interface 50 to a network and then to a network server 63.

The network server 63 is connected via the network to a computed tomography/magnetic resonance imaging (CT/MRI) room 64. In the CT/MRI room 64, a CT/MRI device 65 is connected to a data storage device 66. The data storage device 66 is connected to the network server 63.

A pre-surgery diagnostic image obtained by the CT/MRI device 65 is stored in the data storage device 66. The pre-surgery diagnostic image obtained by the CT/MRI device 65 can be transmitted via the network to external machines.

The network server 63 is also connected to a personal computer 68 (PC hereinafter) of a pathological examiner 67 in the same hospital or in a different hospital. The PC 68 is connected to the data storage device 69. The pathological examiner 67 receives image information transmitted via the network using the PC 68, stores it in a data storage device 69 or displays it on a monitor 70 of the PC 68.

The pathological examiner 67 makes a diagnosis based on the image information, and transmits the result via the network to the operating room 62.

FIGS. 10A and 10B show exemplary images displayed on the TV monitor 49 of the operating room 62, and on the monitor 70 of the PC 68 of the pathological examiner 67.

The TV monitor 49 of the operating room 62 shown in FIG. 10A presents a navigation image 71a, a cytological picture 72a obtained via the beam scanning probe 2, an optical image 73 of a lesion obtained via the surgery microscopic system 44, and descriptive data 74.

A navigation image 71a includes a pointer 75 indicating the spot observed via the beam scanning probe 2, and a cursor 76 through which the operator can work on the image.

FIG. 10B shows images presented on the monitor 70 of the pathological examiner 67. The monitor 70 presents images carried by image information transmitted from the operating room 62, more specifically, a navigation image 71b equivalent to the navigation image 71a and a cytological picture 72b equivalent to the cytological picture 72a.

Next, the operation of this embodiment configured as above will be described.

As shown in FIG. 8, the beam scanning probe 2 has its distal end including the beam scanning head 17 inserted into the bayonet type rigid sheath 42, and the head is guided towards a lesion 6. Signals produced by the beam scanning head 17 are converted by the image processing circuit 22 into an image signal, to be fed to a system control device 47.

On the other hand, the navigation device 45 receives pre-surgery image information, and another information from the light emitting portion 8. Then, the navigation device 45, using the pre-surgery image information and the positional information regarding the spot observed via the beam scanning head 17 of the beam scanning probe 2, superimposes the detected positional information on the pre-surgery image information properly positioned with respect to each other to produce a composite image, and delivers it as output. The operator, while observing a lesion including a tumor via the surgery microscope 43, sets the beam scanning probe 2 in place to focus it on a desired spot of the lesion.

At this moment, when the operator switches ON the remote switch 57a, an operation signal is delivered to the equipment control unit 51 of the system control device 47, to cause the image control unit 52 to effect a selection/combination processing. Then, the navigation device 45 transmits diagnostic CT image information 71a upon which the information regarding the spot observed via the beam scanning probe 2 is superimposed, to the operating room 62 to be displayed on the monitor 49 there as shown in FIG. 10A.

In combination, a microscopic image obtained via the surgery microscope 43 is captured by the TV camera incorporated in the microscope, to be displayed as a monitoring image 73 on the monitor 49. Not to mention, a cytological picture 72a obtained via the beam scanning probe 2 is also displayed on the monitor 49.

As described above, the TV monitor 49 of the operating room 62 presents, prior to surgery, an optically visual image 73 obtained via the surgery microscope 44, a navigation image 71a, a cytological picture 72a of a spot on the lesion whose position is indicated by a pointer 75 (the latest position of the probe) on the navigation image 71a, etc.

When the beam scanning probe 2 captures a desired spot, and the operator switches ON the remote switch 57a, a marker indicating the position of the spot appears on the navigation image 71a.

When the operator confirms the beam scanning probe 2 captures a right spot, and switches ON the remote switch 57b, image information carrying a cytological picture 72a of the spot is recorded in the image file device 48. The image information carrying a cytological picture 72a thus recorded is then transmitted via a network to the PC 68 of the pathological examiner 67 and then stored in the storage unit 69 as appropriate.

The image information transmitted via the equipment control unit 51 and the network interface 50 to the TV monitor 49 to be displayed there, is also transmitted via the network server 63 to the PC 68 of the pathological examiner 67 to be displayed on its monitor 70, and stored in the data storage device 69 so that the examiner can make a diagnosis thereof later.

During this process, the image control unit 52 delivers, in a combined form, all the image signals including a cytological picture 72a obtained via the beam scanning probe 2, a monitoring image 73 obtained via the surgery microscope 43, and a navigation image 71a upon which the spot observed via the beam scanning probe 2 is superimposed. The pathological examiner 67 chooses any desired combination of the images and makes a diagnosis on them.

Then, the pathological examiner 67 determines, based on the information obtained from the images, whether the affected tissue is malignant or not, or checks the information received, or adds a comment thereto by voice using a marker, and transmits the reply via the network to the operating room 62.

The pathological examiner 67 and the operator in the operating room 62 can display any desired spot on the cytological picture 72a and 72b by placing an indicator cursor 76 on the spot and by selecting a marker. The pathological examiner 67 and the operator in the operating room 62 can define the range to be excised or a notable site by line, moving the indicator cursor 76 on the image.

The pathological examiner 67 transmits the diagnosis result with the comment via the same route to the operating room 62 so that the TV monitor 49 there displays the diagnosis result 74 as shown in FIG. 10A. According to this embodiment, the operating room 62 is also connected to the CT/MRI room 64 so that the navigation device 45 can receive image information from a database of pre-surgery diagnostic images stored in the latter.

A CT/MRI image taken prior to surgery is firstly stored in the data storage device 66. The stored data is transmitted via the network to the operating room 62 separated from the CT/MRI room 62, and there the system control device 47 transmits the image data to the navigation device 45, and to the TV monitor 49 for display.

This embodiment ensures following advantages.

According to this embodiment, the operator and the pathological examiner 67 can exchange information of the position of a tumor and its histology on a real time basis, and thus the operator can properly excise the tumor without requiring the presence of the pathological examiner at the site of the surgery, based on the proper diagnosis given to him by the examiner before surgery.

According to this embodiment, in contrast with the current operating site where treatment is applied based on a cytological diagnosis obtained from many biopsied specimens sampled during operation, the operator can directly observe a cytological picture of a lesion on the monitor, transmit the picture to the pathological examiner 67, and receive the diagnosis result from the examiner 67 on a real time basis, which will improve efficiency.

According to this embodiment, the pathological examiner 67 can also transmit his instruction about the site to be examined to the operator, i.e., exchange instructions and opinions about the operation with the operator, which will contribute to the effective selection of procedures for proper diagnosis.

This embodiment is characterized by extracting a pre-surgery diagnostic picture carrying the spot observed via the beam scanning probe 2 and storing the both images of it together with a pre-surgery and post-surgery in a paired fashion, by detecting a relative position of the beam scanning probe 2 with respect to the lesion to be operated, and detecting a correlation position to the diagnostic image with respect to the relative position of the beam scanning probe 2. The embodiment is further characterized by having a means which allows the beam scanning probe 2 to observe a desired spot in the space defined by the pre-surgery diagnostic image, and by having terminals for transmitting/receiving image information to/from external sources, thereby making it possible to manage microscopic images obtained during operation, and site information incorporated in CT/MRI images, that is, cytological pictures in combination with microscopic images, for their timely transmission.

Therefore, according to this embodiment, it is possible to provide the pathological diagnosis of a tumor which was not diagnosed based on a pre-surgery diagnostic image previously taken, to consult a specialist such as a pathologist before surgery, and to properly excise the tumor by efficient procedures based on a proper diagnosis given by the specialist on a real time basis.

Incidentally, the beam scanning probe 2 may include a beam scanning probe using a low-interference beam, instead of a confocal beam scanning probe.

(Third Embodiment)

Figure 12:
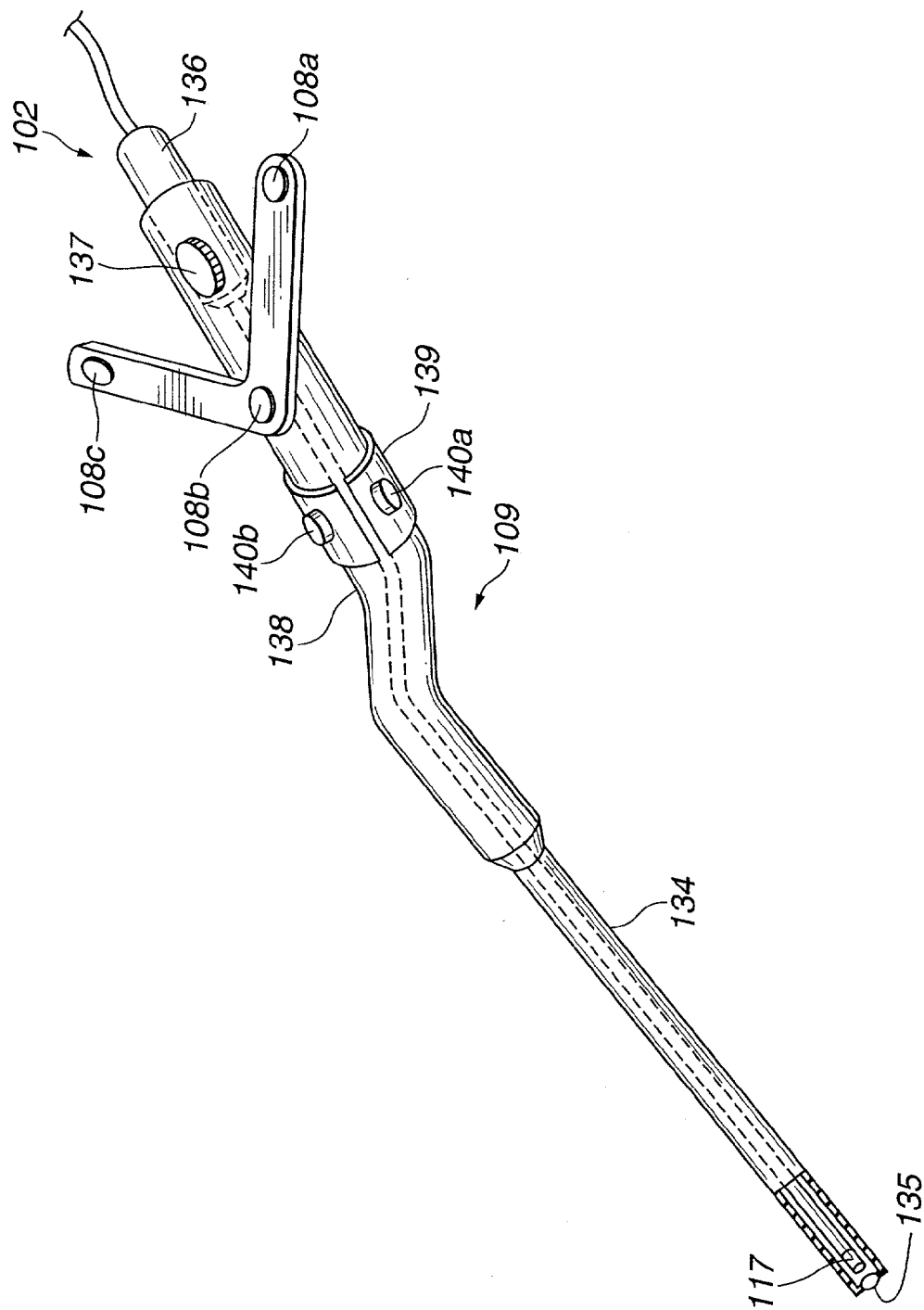
FIG. 12 is a perspective view of a rigid sheath into which a beam scanning probe is inserted.
Figure 13:
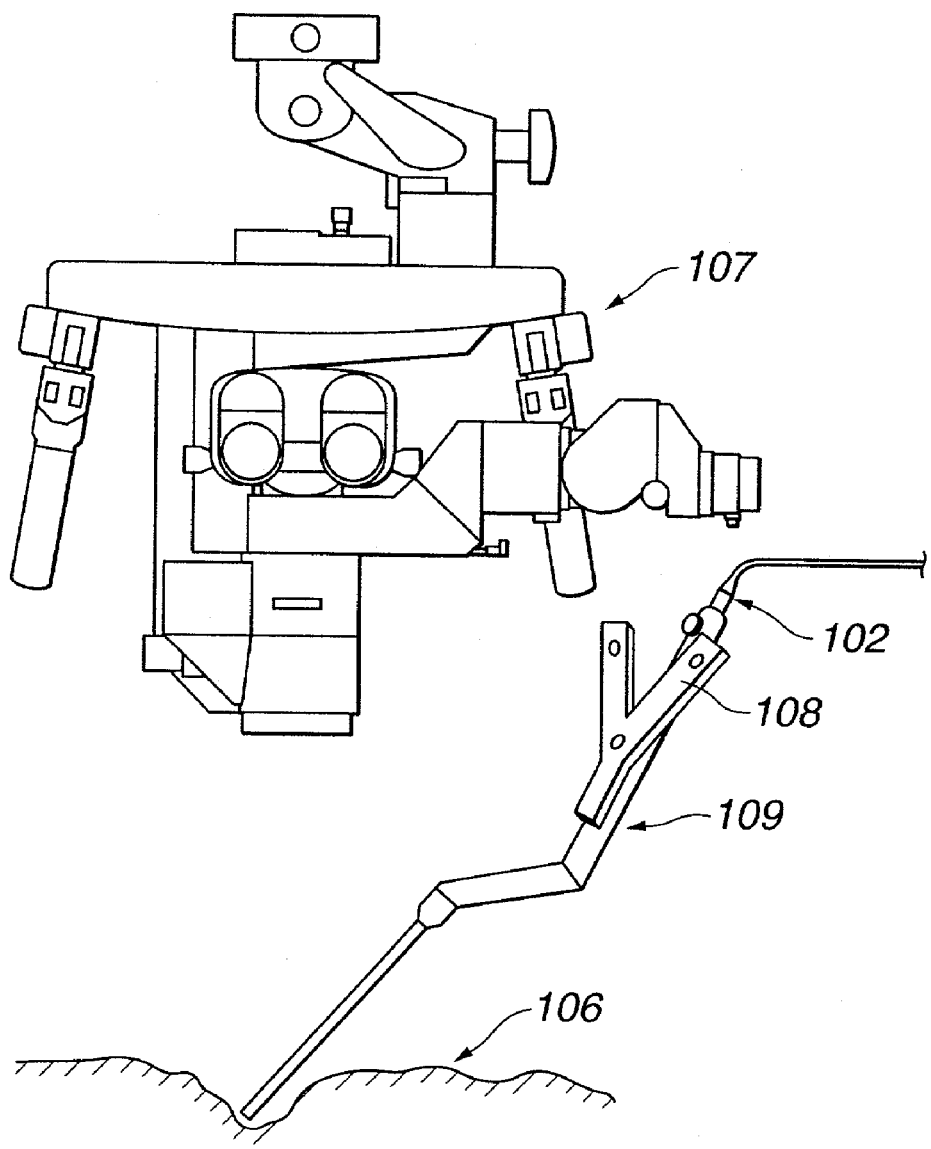
FIG. 13 shows how an image of a lesion is obtained via the beam scanning probe under the observation via a surgery microscope.
Figure 14:
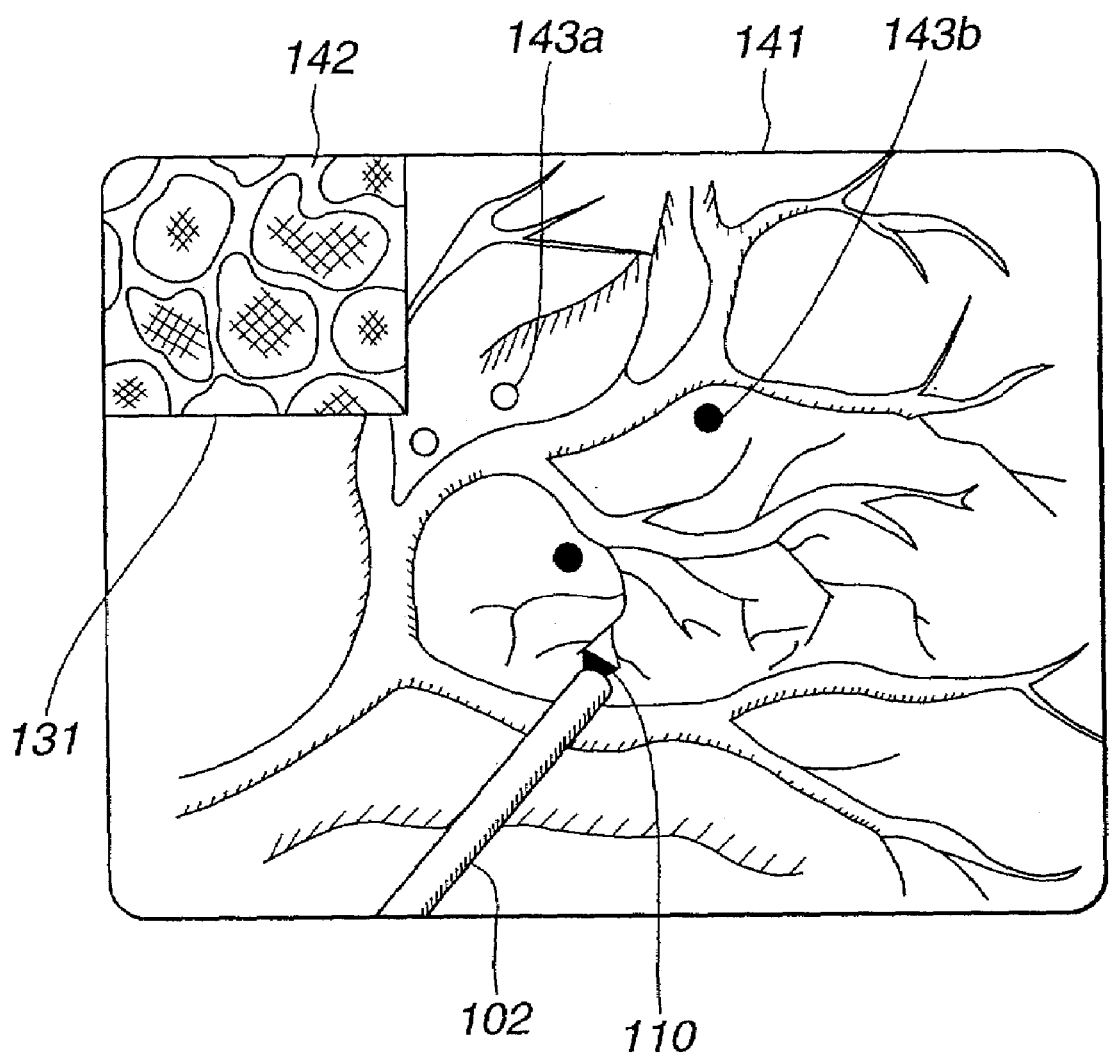
FIG. 14 shows a monitoring image upon which a cytological picture is superimposed.
Figure 15:
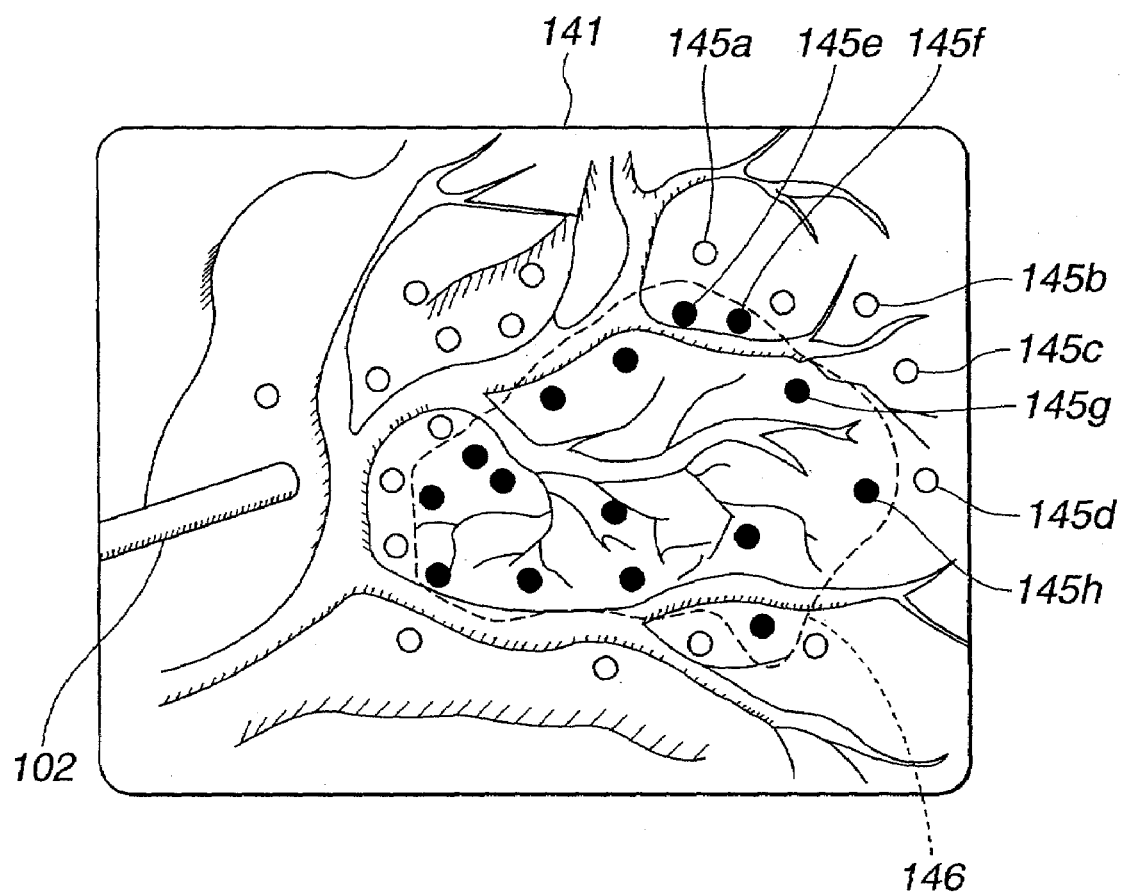
FIG. 15 a monitoring image upon which a plurality of determination result markers are presented.
Figure 16:
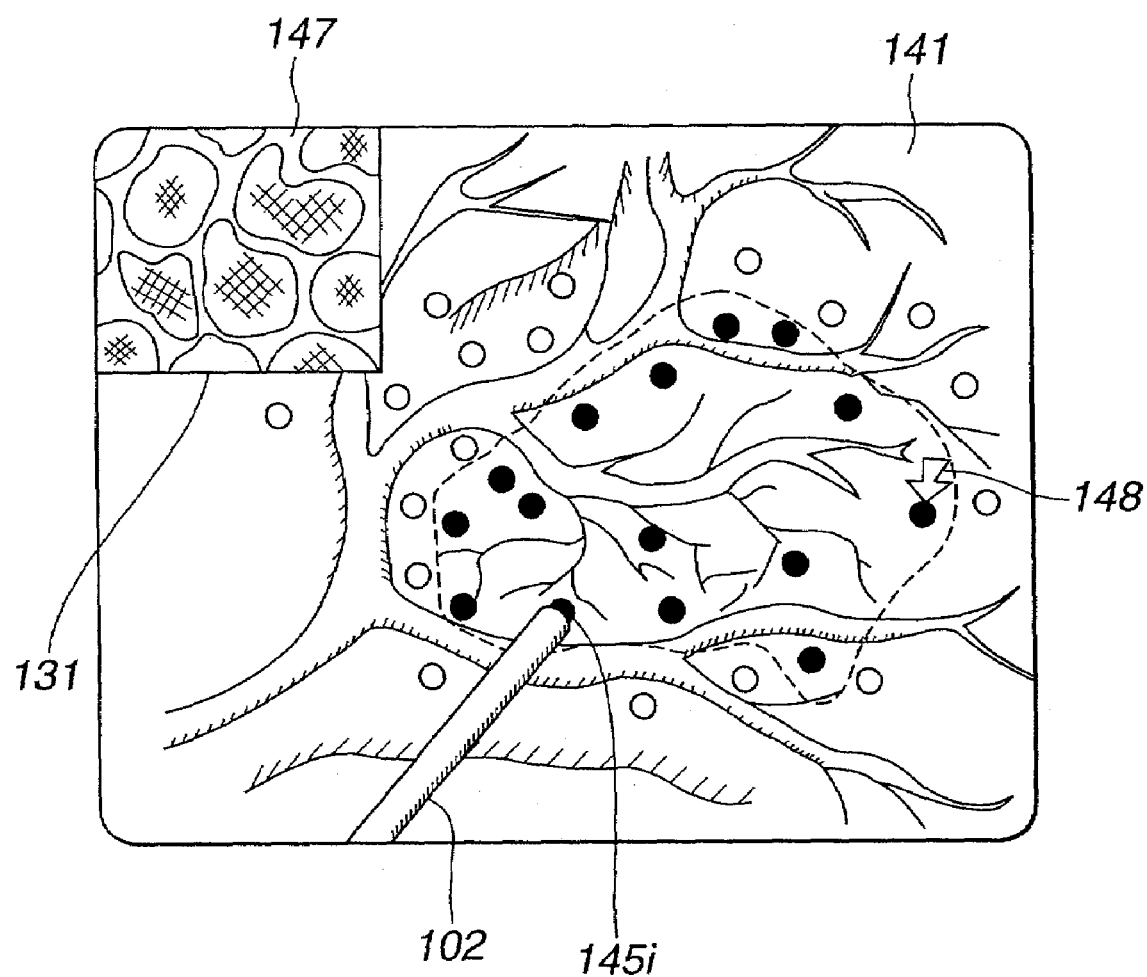
FIG. 16 a renewed display of the same monitoring image together with a cytological picture which was retrieved from an image recording device.

FIGS. 11 to 16 relate to a third embodiment of this invention: FIG. 11 shows the composition of a beam scanning probe system representing a third embodiment; FIG. 12 is a perspective view of a rigid sheath into which a beam scanning probe is inserted; and FIG. 13 shows how an image of a lesion is obtained by the beam scanning probe under the observation via a surgery microscope. FIGS. 14 to 16 relate to images displayed on the monitor of the beam scanning probe system for surgery: FIG. 14 shows a monitoring image upon which a cytological picture is superimposed; FIG. 15 a monitoring image upon which a plurality of detection markers are presented; and FIG. 16 a renewed display of the same monitoring image together with a cytological picture which was retrieved from an image recording device.

As shown in FIG. 11, a beam scanning probe system for surgery 101 representing the third embodiment of this invention comprises a confocal beam scanning probe 102 (simply beam scanning probe hereinafter) for obtaining a confocal optical image of a test organ; an observation system 103 to which the proximal end of the beam scanning probe 102 is detachably connected, and which provides a laser beam to the beam scanning probe 102, and applies image processing to light carrying information about the test organ, more specifically to light returning from the cranial lesion; monitors 104a and 104b which receive video signals from the observation system 103 and display a confocal image and other images derived therefrom; and a navigation device 105 for detecting the spot observed via the beam scanning probe 102.

The beam scanning probe system for surgery 101 further comprises a surgery microscope 107 which gives an enlarged view of a cranial lesion to be operated on (see FIG. 13). The beam scanning probe 102 of this embodiment is inserted, prior to use, into a rigid sheath 109 equipped with a light emitting portion 108 for positional detection as shown in FIG. 12.

The observation system 103 incorporates a laser beam source 111. A laser beam provided by the laser beam source 111 is introduced via a converging lens 112 into a single mode fiber 113.

The laser beam passing through the single mode fiber 113 is conveyed via a coupler section 114 inserted midway and a connector 115b jointed to a connector socket 115a to another single mode fiber 116 running within the beam scanning probe 2. The single mode fiber 116 is connected, at the distal end (tip) of the probe, to a beam scanning head 117 which scans the beam. A laser beam (delivered via a converging lens 135 attached to the distal end of the rigid sheath 109) is scanned by the beam scanning head 117 over a two-dimensional space around a lesion 106 of a test organ.

Light reflected by the lesion 106 impinges (via the converging lens 135 and the beam scanning head 117) on the distal end of the single mode fiber 116, and passes through the same path in the reverse direction towards the coupler section 114. Part of the light guided to the coupler section 114 is diverged into a third single mode fiber 118.

The distal end of the single mode fiber 116 has a sufficiently small surface area. A laser beam emanating from the distal end of the single mode fiber 116 is converged via an optical system including the converging lens 135 onto the lesion 106. In this process, the laser beam emanating from the distal end of the single mode fiber 116 is focused into a spot at a position which allows reflected light therefrom to take a confocal relation to the distal end of the single mode fiber 116 via the intervening optical system.

Further, light reflected by the lesion 106 is converged by the optical system including the converging lens 135. However, out of the reflected light, only the component that has been reflected from the focusing point is allowed to enter the distal end of the single mode fiber 116. Briefly, the observation system 103 is configured such that it allows only light (also called returning light) reflected from the confocal position to enter the distal end of the single mode fiber 116.

The returning light is transmitted via the proximal (rear) end of the single mode fiber 118 to an optical sensor 119. A damper 120 is placed opposite to the distal end of the single mode fiber 118. The damper 20 is for attenuating light emanating from the distal end of the single mode fiber 118 (that is, the damper forms a blind end where no reflection of light occurs).

A detection signal which is produced as a result of photoelectric conversion at the photo sensor 119 is amplified by an amplifier 121 to be fed to an image processing circuit 122. The image processing circuit 122 is for reconstructing an image from detection signals using scan control signals delivered by a beam scan control circuit 123 which controls the beam scanning head 117 and outputs the image signals.

The navigation device 105 includes a digitizer 125 for positional detection. The digitizer 125 detects, for example, infra-red rays emitted by a light emitting portion 108, and delivers a position signal obtained from the rays to the navigation device body 126.

The navigation device body 126 also receives signals carrying, for example, an image of a cranial lesion (including the lesion 106 to be operated on) delivered by a surgery microscope 107, or by a TV camera 127 placed close to the microscope both of which serve as an image acquiring means.

The navigation device body 126 delivers image signals carrying a microscopic image of the cranial lesion. At the same time, it detects the position of the light emitting portion 108 shown in FIG. 12 via the digitizer 125, and further determines the position of the site of cranial lesion observed via the beam scanning head 117 which is by a predetermined distance in a predetermined direction apart from the light emitting portion 108, and produces a navigation image.

The observation system 103 is configured such that image signals from the image processing circuit 122 and the navigation device body 126 are combined at a mixer 124 which delivers the combination result to a monitor 104a to produce a navigation image therefrom for display. The image processing circuit 122 is connected to the monitor 104b and an image recording device 130.

Image signals from the image processing circuit 122 are delivered to the monitor 104b which displays, based on the signals, a cytological picture 131 of the lesion obtained via the beam scanning probe 102. The image recording device 130 stores the cytological picture 131 delivered via the image processing circuit 122.

The navigation device body 126 is connected to a determination result feeding device 132. The determination result feeding device 132 is for feeding the determination result regarding the cytological picture 131 presented on the monitor 104b.

FIG. 12 shows the overview illustrating the shape of the beam scanning probe 102 and the bayonet type rigid sheath 109.

The hollow, bayonet type rigid sheath 109 comprises a rigid handle portion 138 including at least two bends, and a constricted sheath portion 134 (sheath insertion segment) which is obtained by constricting the distal end of the handle portion 138 to give a rigid tube having a smaller diameter.

The rigid sheath 109 receives the insertion of the beam scanning probe 102 from the proximal (rear) end of its handle portion 138. The beam scanning probe 102 is properly positioned with respect to the rigid sheath 109 such that its distal end is close and opposite to the converging lens 135 attached to the distal end of the constricted sheath portion 134, and then the joining portion 136 of the beam scanning probe 102 is detachably fixed by a fixation pin 137.

The rigid sheath 109 has on a rear part of the handle portion 138 the light emitting portion 108 which helps the digitizer 125 to detect the position of observation. The light emitting portion 108 carries a number of light emitting elements 108a–108c which emit infra-red rays.

The handle portion 138 has a remote switch holder 139 attached thereto. The remote switch holder 139 carries at least two remote switches 140a and 140b.

The remote switches 140a and 140b are connected via a signal line 140c to the navigation device body 126 (see FIG. 11). Incidentally, the beam scanning probe 102 has the connector 115b of its proximal end detachably jointed to the connector socket 115a of the observation system 103. The connector 115b also includes connector pins (not illustrated here) connected to signal lines leading to the beam scanning head 117. The beam scanning probe 102 is thus connected via the connector socket 115a to the beam scan control circuit 123.

The embodiment configured as above allows one to register into the image recording device 130 a microscopic image of a cranial lesion to be operated on, and a navigation image upon which a spot to be observed via the beam scanning probe 102 is superimposed and a cytological picture 131 actually obtained via the beam scanning probe 102 presented in a paired fashion, and to present those images on the monitor 104a.

The operation of the embodiment configured as above will be described below.

The beam scanning probe 102 has its connector 115b connected to the observation system 103 as shown in FIG. 11. The navigation device 105 is also set in place as shown in FIG. 11. Then, the beam scanning head 117 of the beam scanning probe 102 is inserted into the rigid sheath 109, and guided to a lesion 106 to be operated on, under the observation via the surgery microscope 107 as shown in FIG. 13.

The TV camera 127 takes a picture of the lesion 106, and the picture of the lesion 106 is displayed via the navigation device body 126 on the monitor 104a as a navigation image 133 as shown in FIG. 11. The navigation image 133 includes a pointer 110. The pointer indicates the observation point of the beam scanning head 117 of the beam scanning probe 102 which is responsible for obtaining a microscopic view of the lesion 106 (or of a desired spot on the lesion).

As shown in FIG. 11, confocal optical signals obtained by the beam scanning head 117 of the beam scanning probe 102 from the observation point is converted by the image processing circuit 122 into video signals carrying a confocally scanned image, or in this case a cytological picture 131, which are then fed to the monitor 104b for display.

Then, when the remote switch 140a or the remote switch 140b as shown in FIG. 12 is depressed, the beam scanning probe 102 obtains a cytological picture 131 of a desired point to store it in the image recording device 130, and the navigation device body 126 determines the coordinate of the observation point.

The image signals carrying the cytological picture 131 are combined with the image signals carrying the navigation image 133 to be fed to the image recording device 130. Then, it is possible to display the two images simultaneously on the monitor 104a.

FIG. 14 shows exemplary images on the monitor 104a.

As shown in FIG. 14, the monitor 104a presents an image 141 of a lesion taken by the TV camera 127 connected to the navigation device body 126 or by a TV camera not illustrated here but incorporated in the microscopic system, and a cytological picture 142 (131) in an inset screen placed on the image 141 of the lesion.

The cytological picture 131 shown in the monitor 104b is submitted to the pathological examiner who determines its malignancy, and transmits the diagnosis result via the determination result feeding device 132 to the navigation device body 126.

Then, the determination results (diagnoses) from the pathological examiner are transformed by the navigation device body 126 into appropriate markers: a pointer 110 indicating the observation spot is turned into an appropriate marker depending on the diagnosis determined for the spot as represented by a diagnosis marker 143a or 143b. For example, when the pathological examiner finds the tissue of a spot malignant based on the cytological picture 142 (131) thereof, the pointer turns into a malignancy marker 143b, whereas when the pathological examiner finds the tissue of the same spot benign based on the cytological picture 142 (131) thereof, the pointer turns into a benign marker 143a. Thus, markers different in shape and color appear on different spots of the microscopic image 141 of the lesion, depending on the pathological condition of those spots.

The navigation device body 126 determines the extent of malignant parts based on the distribution of malignancy markers 143b or of benign maker 143a, and causes the monitor to display the malignant extent as shown in FIG. 15.

FIG. 15 shows an exemplary image on the monitor 104a carrying plural diagnosis markers.

The navigation device body 126 determines the extent of malignant parts 146 based on the distributions of malignancy markers 145e to 145h as well as of benign markers 145a to 145d.

The malignant extent 146 can be determined by drawing a boundary line between an adjacent malignancy marker and benign marker (for example, between a malignancy marker 145a and a malignancy marker 145e) shifting the boundary towards the benign marker or towards the malignancy marker depending on the diagnosis result provided by the determination result feeding device 132. Based on this result, the operator can determine the parts to be excised, or can check what fraction of a malignant tumor is left intact.

The navigation device body 126 can cause a renewed display of a cytological picture 147 stored in the image recording device 130 for each marker point as shown in FIG. 16.

FIG. 16 shows an exemplary image on the monitor 104a where a cytological picture 147 is retrieved from the image recording device 130 for renewed display.

When the spot of observation via the beam scanning probe 102 is made coincident with a spot indicated by a marker 145i, or when an indication cursor 148 is placed on the latter spot using a marker control means not illustrated here, the navigation device body 126 allows a cytological picture 147 of the spot in question to be retrieved from the image recording device 130 for display. This allows the operator to recheck the spot previously diagnosed.

Consequently, the present embodiment ensures following advantages.

According to this embodiment, it is possible to smoothly perform pathological diagnosis and operation. This embodiment will reduce time required for operation which will contribute for relieving the operator and the patient of strain and pain. More specifically, according to this embodiment, because it is possible to display/record/replay a cytological picture of a lesion in combination with a microscopic image thereof, the operator can easily correlate the image information obtained from the cytological picture with the site information. According to this embodiment, because the extent of a lesion can be precisely defined, the operator can easily determine hot to excise the lesion.

(Fourth Embodiment)

Figure 17:
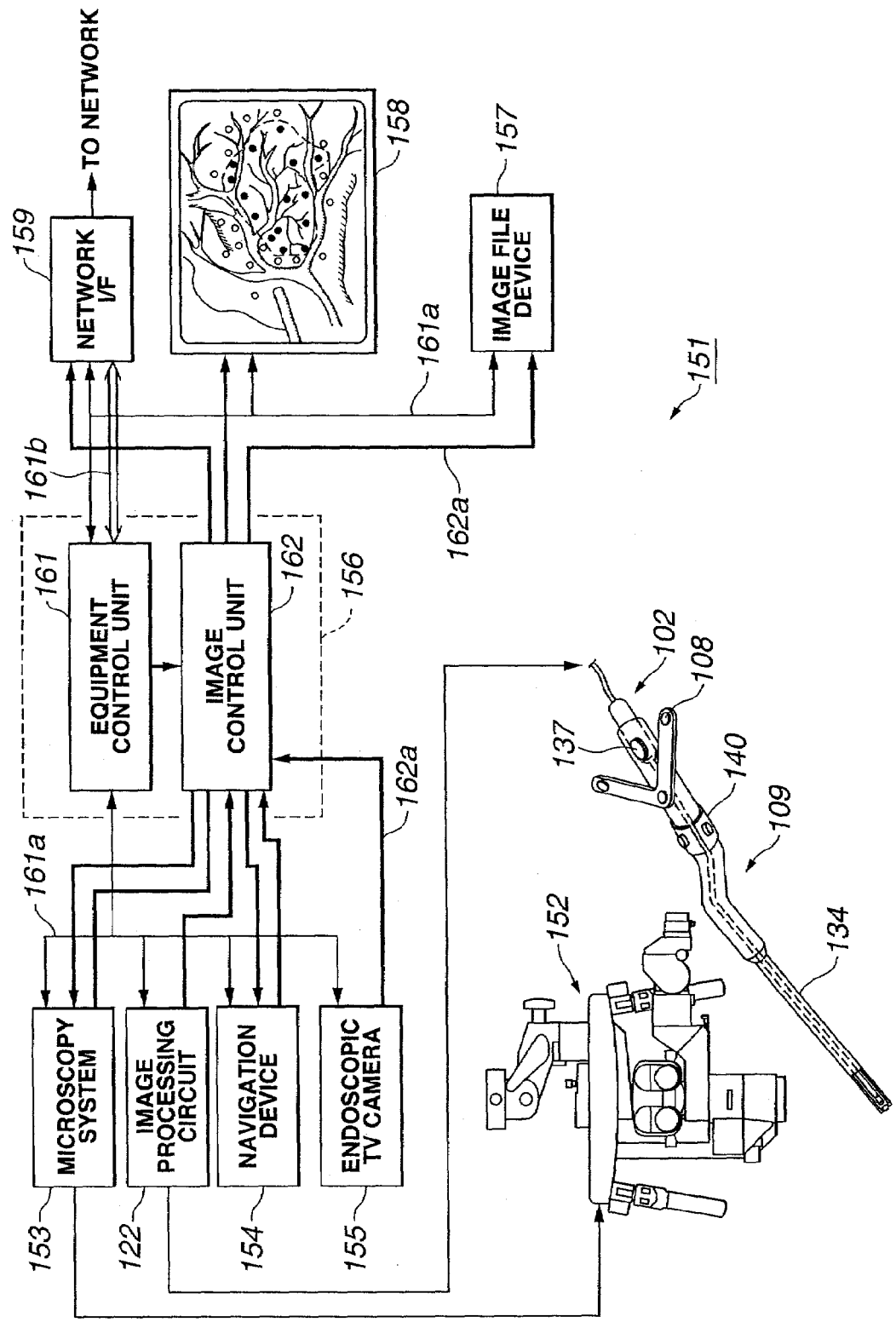
FIG. 17 shows the composition of a beam scanning probe system representing a fourth embodiment of this invention.
Figure 18:
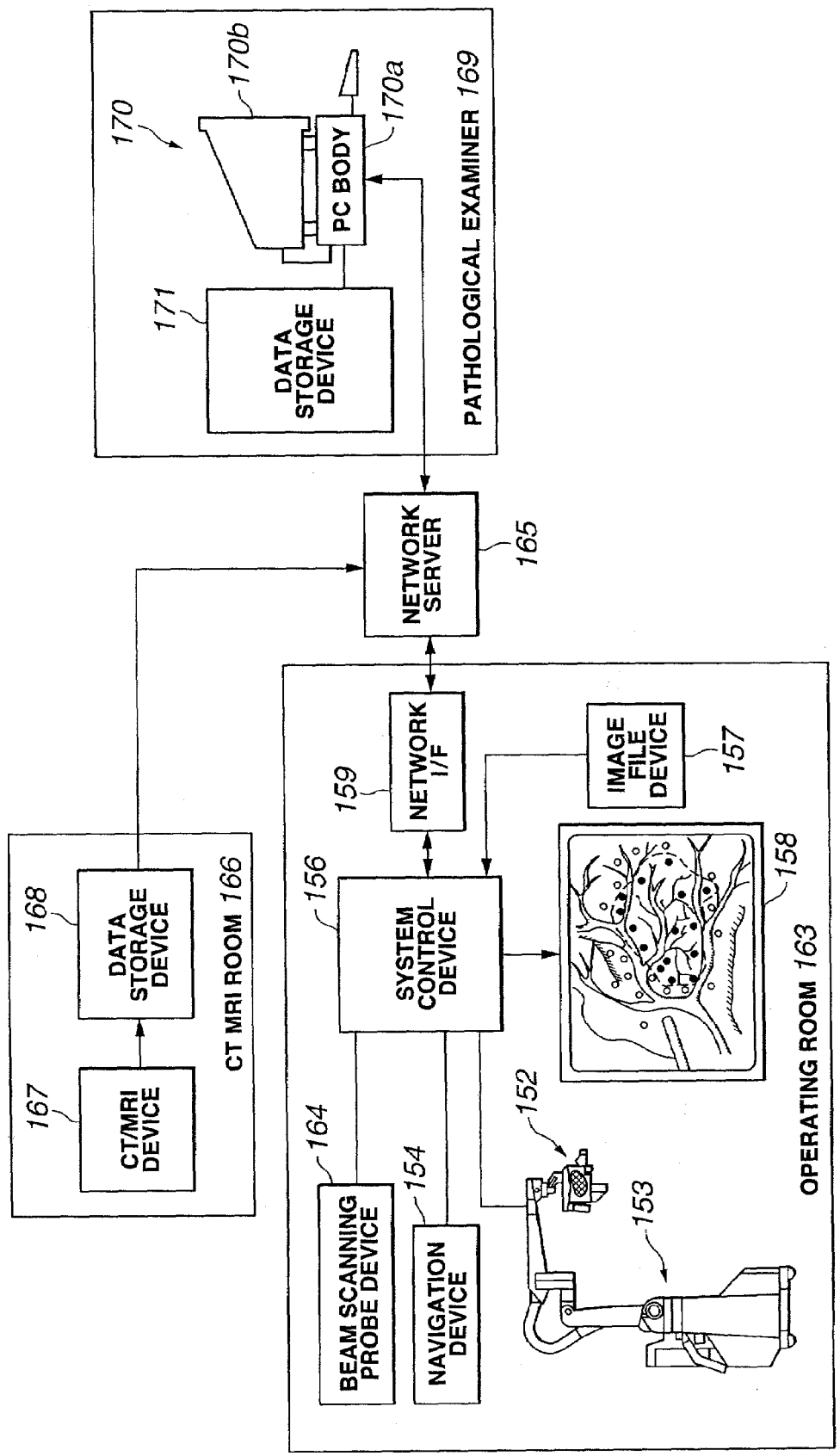
FIG. 18 shows the composition of the beam scanning probe system used in a hospital, or used between hospitals.

FIGS. 17 and 18 relate to a fourth embodiment of this invention: FIG. 17 shows the composition of a beam scanning probe system representing a fourth embodiment of this invention; and FIG. 18 the composition of the beam scanning probe system used in a hospital, or used between hospitals.

The fourth embodiment represents utilization of the beam scanning probe system for surgery in a hospital or between hospitals.

As shown in FIG. 17, the beam scanning probe system 151 representing the fourth embodiment of this invention comprises a rigid sheath 109 receiving the insertion of a beam scanning probe 102; a surgery microscope 152; a system control device 156 to which the surgery microscope 152 and the beam scanning probe 102 are connected via an image processing circuit 122 and a microscopy system 153 respectively, as well as a navigation device 154 and an endscopic TV camera 155; an image file device 157 which is also connected to the system control device 156; a TV monitor 158; and a network interface 159 (network IF hereinafter) connected to a network.

The system control device 156 controls equipment connected thereto including the microscopy system 153 and others (systems and devices), and comprises an equipment control unit 161 responsible for transmitting image data via the network I/F 159 to external machines, and for receiving image data from external machines, and an image control unit 162 responsible for controlling image signals handled by equipment connected to the system control device 156.

The equipment control unit 161 is connected via a local communication line 161a such as RS232C to the microscopy system 153, the image processing circuit 122, the navigation device 154, an endscopic TV camera 155, the image file device 157, the TV monitor 158 and the network I/F 159.

The image control unit 162 is connected via an image communication line 162a to the microscopy system 153, image processing circuit 122, navigation device 154, endscopic TV camera 155, image file device 157, TV monitor 158 and network I/F 159. The image control unit 162 controls such that video signals from the beam scanning probe 102 and endscopic TV camera 155 are delivered to the image file device 157 and TV monitor 158.

On the other hand, the equipment control unit 161 is connected via a local communication line 161a such as RS232C to the above-described microscopy system 153, image processing circuit 122, navigation device 154, endscopic TV camera 155, network I/F 159, TV monitor 158 and image file device 157, so as to alter the setting of those equipment.

The equipment control unit 161 is connected via a data line 161b to the network I/F 159. The equipment control unit 161 transmits/receives image signal data, voice data, computer data, etc., via the network I/F 159 to, and from external sources connected to the network.

Incidentally, the process during which signals captured by the beam scanning head 117 of the beam scanning probe 102 are converted into an image is the same as in the third embodiment. The other configuration is the same as in the first embodiment described above.

The beam scanning probe system for surgery 151 configured as above serves as a beam scanning probe system for surgery used in a hospital or between hospitals as depicted in FIG. 18.

FIG. 18 shows the composition of the beam scanning probe system used in a hospital, or used between hospitals.

In an operating room 63, a surgery microscopy system 153 approximately the same with what is described above with reference to FIG. 17, a (confocal) beam scanning probe device 164, a navigation device 154, a TV monitor 158 and others are connected to a system control device 156. Incidentally, the beam scanning probe device 164 is a device comprising the beam scanning probe 103 inserted into the rigid sheath 109 as shown in FIG. 17, and the image processing unit 122.

The system control device 156 is connected via the network I/F 159 to a network server 165. The network server 165 is connected via the network to a CT/MRI room 166. In the CT/MRI room 166, a CT/MRI device 167 is connected to a data storage device 168. The data storage device 168 is connected to the network server 165.

The CT/MRI device 167 stores pre-surgery diagnostic images in the data storage device 168. Moreover, the CT/MRI device 167 can transmit the pre-surgery diagnostic images via the network to external sources.

The network server 165 is also connected to a personal computer 170 (PC hereinafter) of a pathological examiner 169 in the same hospital or in a different hospital. The PC 170 is connected to the data storage device 171. The pathological examiner 169 receives image information transmitted via the network using the PC 170, stores it in a data storage device 171 or displays it on a monitor 170b of the PC. The number 170a represents the body of the PC 170. The pathological examiner 169 makes a diagnosis based on the image information, and transmits the result via the network to the operating room 163.

Next, the operation of this embodiment will be described.

According to this embodiment, the flow of image signals is approximately the same with that of the third embodiment described above: in both cases image signals are centrally controlled by the image control unit 162 of the system control device 156.

Referring to FIG. 17, the surgery microscope 152 takes a picture of, for example, a cranial lesion (or a lesion 106 to be operated on) via a TV camera not illustrated here but incorporated therein. The image signals from the TV camera are processed by the image processing circuit 122 into video signals, which are then transmitted via the image control unit 162 of the system control device 156 to the navigation device 154.

The navigation device 154 adds thereto information regarding a cytological picture obtained from a spot by the beam scanning probe 102 and information regarding the position of the spot, and transmits the resulting video signals via the image control unit 162 to the monitor 158 to give a monitoring display.

The cytological picture captured by the beam scanning probe 102 and processed by the image processing circuit 122 is transmitted as image data via the image control unit 162 to the network I/F 159 and then to different sites in the same hospital or in a different hospital, and at the same time stored in the image file device 157.

On the other hand, in the operating room 163, determination data including the diagnosis made on the cytological picture are received via the network, and transmitted via the equipment control unit 161 of the system control device 156 to the navigation device 154.

The navigation device 154, based on the determination data thus transmitted, constructs video data carrying a descriptive image 141 which includes, in addition to a monitoring image, benign markers 145a, malignancy markers 145e, and a demarcation line 146 defining the malignancy extent like those as described above with reference to FIG. 15 of the third embodiment, and transmits the data via the image control unit 162 to the monitor 158 for display. On the other hand, the equipment control unit 161 is responsible for the central control of different equipment connected thereto, and for altering the setting of those equipment, and switching the entry and exit of video signals among different equipment.

As seen from above, according to this beam scanning probe system for surgery, because the equipment control unit 161 and the image control unit 162 of the system control device 156 are responsible for the central control of different equipment, it is possible to transmit at will images obtained via the microscopic system 153 and the endscopic TV camera 155, or pre-surgery diagnostic images obtained in the CT/MRI room 166 as shown in FIG. 18 via a network to the monitor 158 for display.

Referring to FIG. 18, in the operating room 163, as described above with respect to the third embodiment, one can observe treatment currently undertaken on a microscopic image provided via the microscopy system 153 under the control of the navigation device 154, and a cytological picture of a lesion provided by the beam scanning probe 164.

The TV monitor 158 of the operating room 163 can present a microscopic image, a navigation image, a cytological picture, and a pre-surgery diagnostic image transmitted from the CT/MRI room 166.

At the moment when the beam scanning probe 164 captures a desired spot, the operator depresses the remote switches 140a and 140b in the same manner as in the third embodiment. Then, a pointer 110 appears on the monitoring image as discussed above with respect to FIG. 15, and image information regarding a cytological picture of the spot is recorded. The image information carrying the cytological picture thus recorded is transmitted via the network to a PC 170 of the pathological examiner 169, and stored in a storage unit 171 as appropriate.

The PC monitor 170b of the pathological examiner 169 displays the cytological picture not illustrated here retrieved from the storage unit 171. The pathological examiner 169 determines the malignancy of the lesion based on the cytological picture, and transmits the resulting information via the network to the operating room 163.

In the operating room 163, the information provided by the pathological examiner 169 is analyzed for each spot of observation: the spots are marked as benign or malignant depending on the corresponding information, and depicted as such on a monitoring image together with the malignant extent 146.

Consequently, according to the fourth embodiment, it is possible to undertake diagnosis/operation without requiring the presence of a pathological examiner on the site, in addition to the advantages obtained from the third embodiment.

(Fifth Embodiment)

Figure 19:
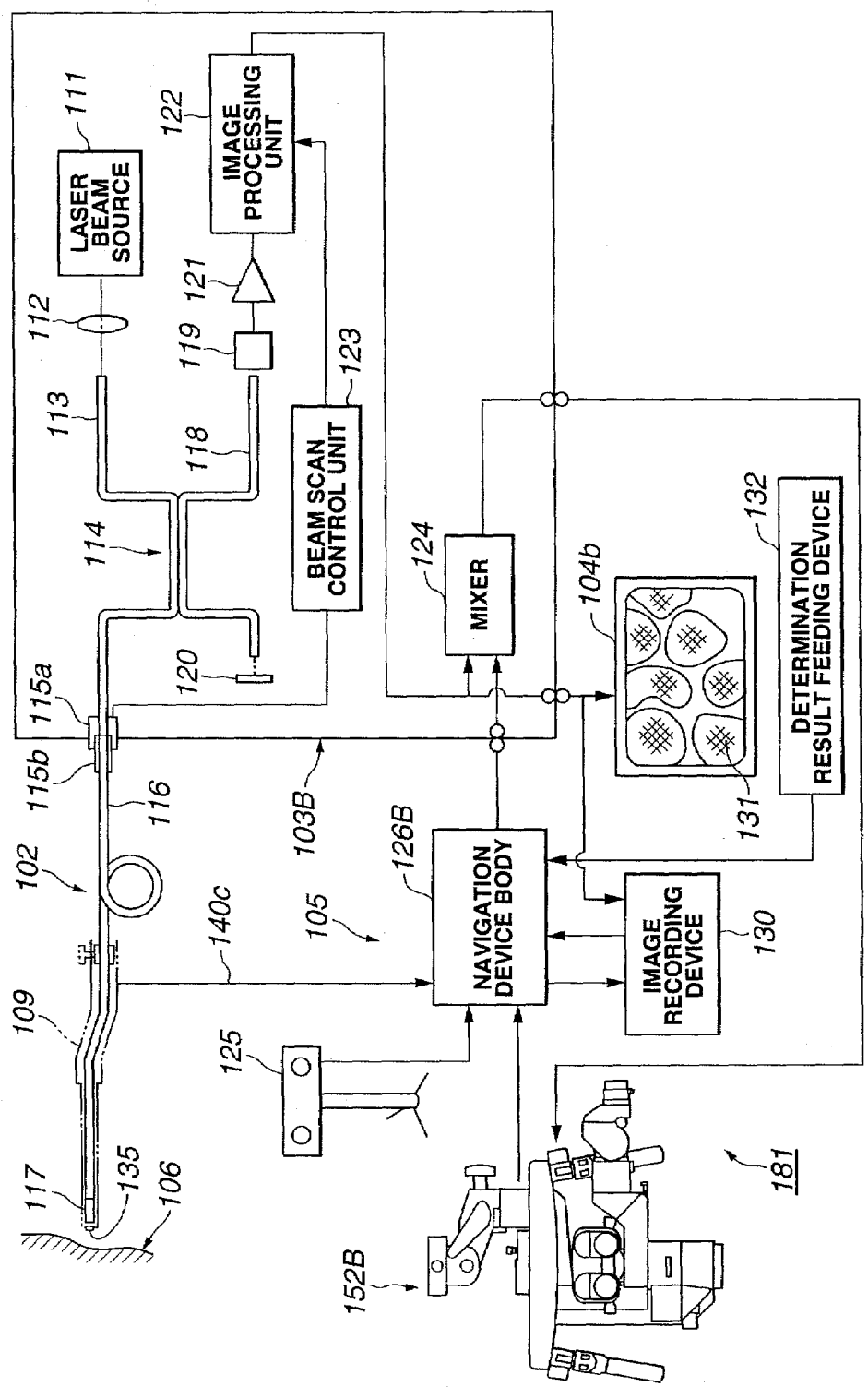
FIG. 19 shows the composition of a beam scanning probe system representing a fifth embodiment of this invention.
Figure 20A:
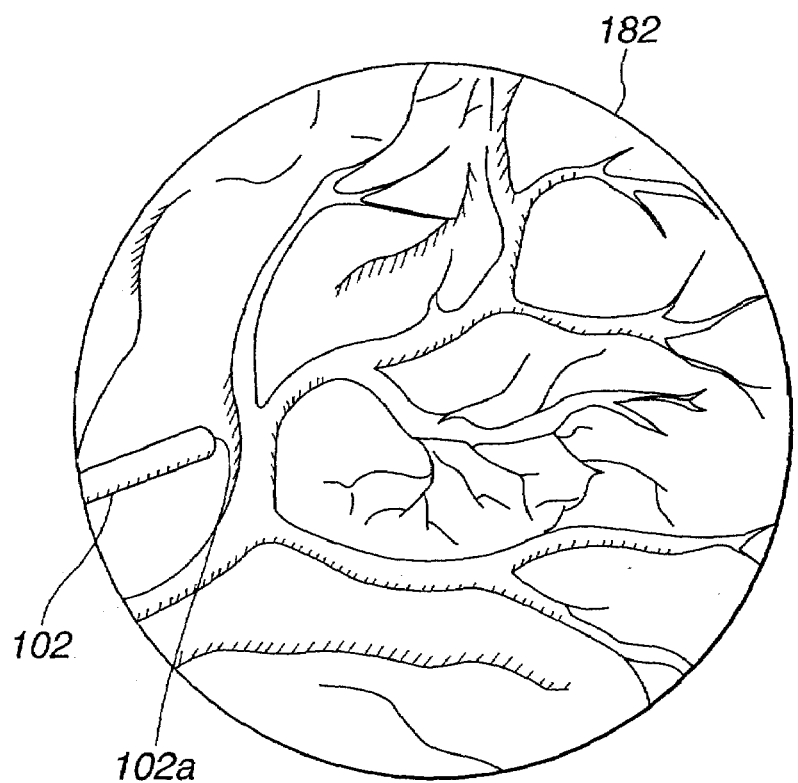
FIG. 20A shows a monitoring image of an optical visual area under a surgery microscope.
Figure 20B:
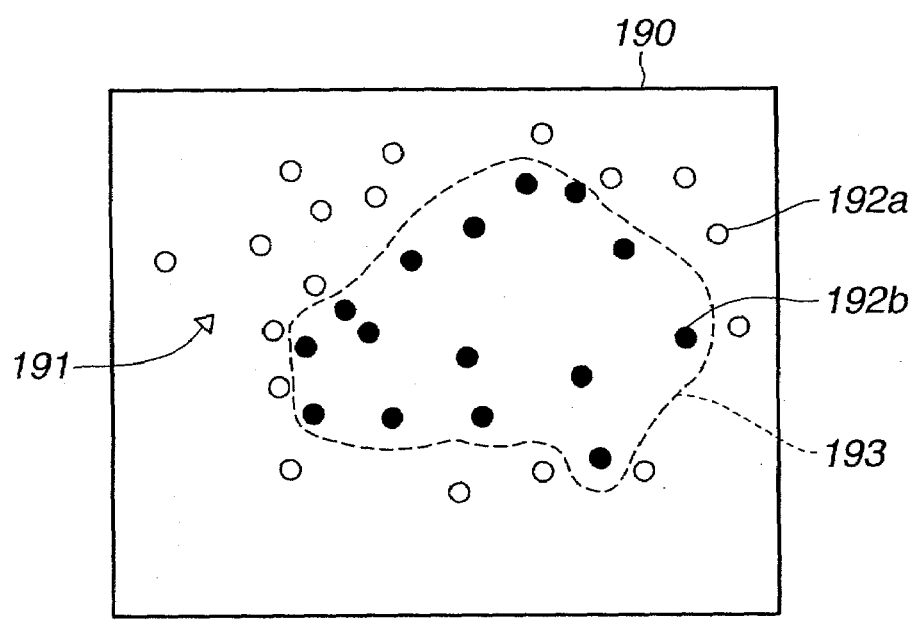
FIG. 20B shows a navigation image presented on an overlay monitor of the surgery microscope.
Figure 21:
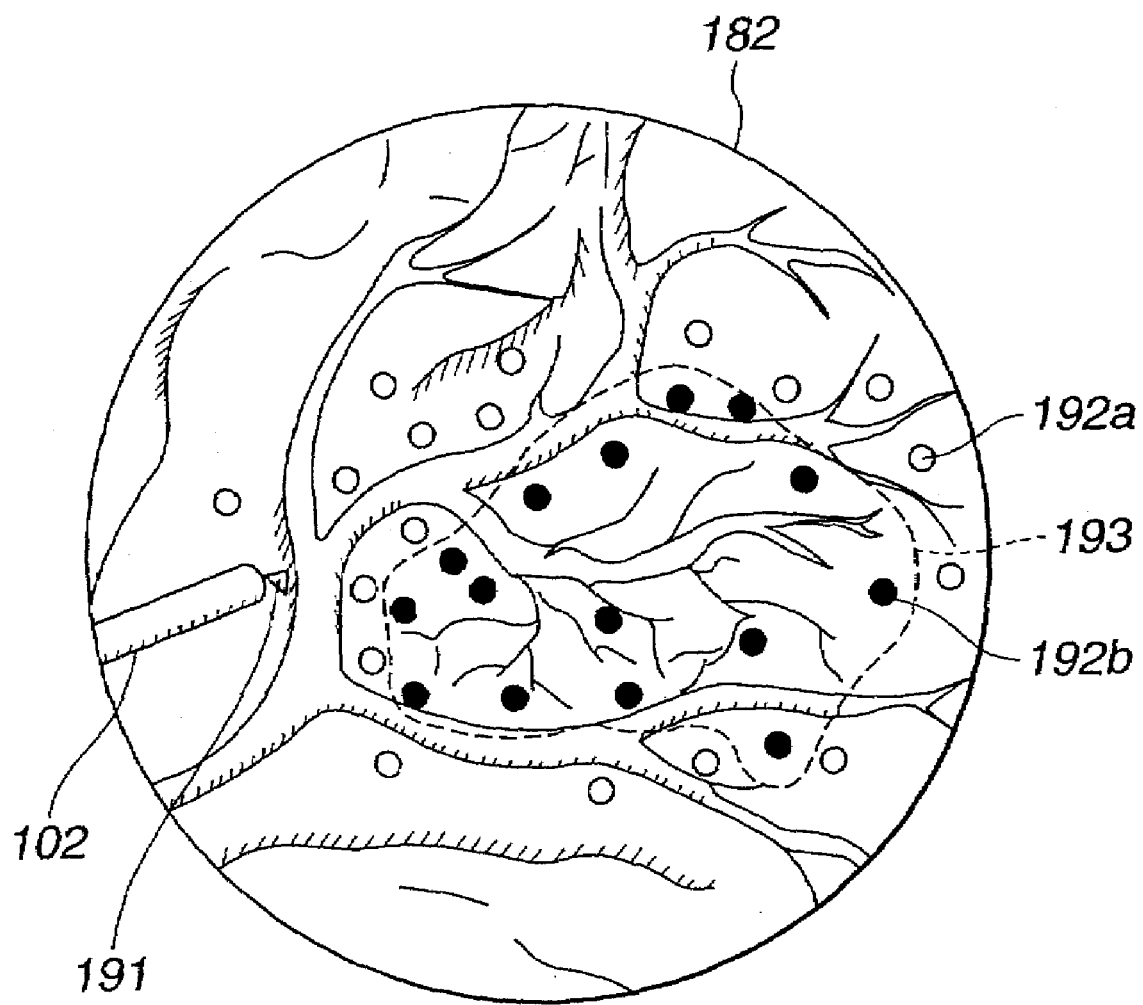
FIG. 21 shows an optical visual area of the surgery microscope in which a navigation image is superimposed on a monitoring image.

FIGS. 19 to 21 relate to the fifth embodiment of this invention: FIG. 19 shows the composition of a beam scanning probe system representing a fifth embodiment of this invention; FIG. 20A shows an optical visual area under a surgery microscope; FIG. 20B shows a navigation image presented on an overlay monitor of the surgery microscope; and FIG. 21 shows an optical visual area viewed via the surgery microscope where the navigation image is superimposed on a monitoring image.

In contrast with the third and fourth embodiments where the positional information, the determination result provided by the pathological examiner, the malignant extent are superimposed on a monitoring image presented on the monitor, according to the fifth embodiment, the positional information, the determination result from the pathological examiner and the malignant extent are provided into an optical visual area of a surgery microscope. The fifth embodiment is similar to the third embodiment in other features, and thus the explanation of those features will be omitted, and the same symbols will be attached to the equivalent elements.

As shown in FIG. 19, the beam scanning probe system 181 for surgery representing the fifth embodiment of this invention comprises a surgery microscope 152B, and a navigation device body 126B which causes the positional information, the determination result provided by the pathological examiner, and the malignant extent to be provided into an optical visual area of the surgery microscope 152B.

The surgery microscope 152B incorporates a TV camera not illustrated here which defines an optical visual area, and which is connected to the navigation device body 126B so that signals defining the visual area can be transmitted to the navigation device body 126B.

The surgery microscope 152B further comprises an overlay monitor in an optical system not illustrated here but involved in the determination of the visual area. The overlay monitor is connected to a mixer 124 of the observation system 103B so that it can receive video signals from the mixer 124.

The navigation device body 126B causes the position of the surgery microscope 152B with respect to a lesion to be detected, and determines by calculation the position of the distal end of the beam scanning probe 102 in the visual area of the surgery microscope 152B.

The navigation device body 126B further causes the calculated position of the distal end of the beam scanning probe 102 to be displayed as a pointer on the overlay monitor of the surgery microscope 152B, and generates information carrying a navigation image where each observation spot is marked malignant or benign as the case may be dependent on the determination results provided by the pathological examiner via the determination result feeding device 132, and transmit it to the mixer 124 of the observation system 103B.

The navigation device body 126B further determines the extent of malignant parts based on the distribution of diagnosis markers, and causes the malignant extension thus determined to be superimposed upon the navigation image.

The observation system 103B is similar in configuration to that of the third embodiment excepting the image recording device 130.

According to the embodiment configured as above, it is possible to display the positional information, the determination result from the pathological examiner and the malignant extension in the optical visual area of the surgery microscope 152B.

Next, the operation of the present embodiment will be described.

The surgery microscope 152B defines an optical visual area 182 around a lesion, for example, as shown in FIG. 20A. Then, information carrying the monitoring image of the lesion is transmitted to the navigation device body 126B.

The navigation device body 126B detects the position of the surgery microscope 152B with respect to the lesion, and generates information carrying a navigation image 190 where a pointer 191 indicating the position of the distal end of the beam 102a of the scanning probe 102 in the visual area of the surgery microscope 152B to cause the image to be displayed on the overlay monitor of the surgery microscope 152B.

The mixer 124 of the observation system 103B transmits the video signals from the navigation device body 126B to the overlay monitor of the surgery microscope 152B to present the navigation image over the visual area 182 of the surgery microscope 152B. If the remote switch 140a or 140b of the beam scanning probe 102 is depressed at this moment, a cytological picture 131 obtained by the beam scanning probe 102 from a spot thus chosen is displayed on the monitor 104b as well as recorded in the image recording device 130 (see FIG. 19).

The pathological examiner determines the malignancy of the tissue on the spot by observing the cytological picture 131 thereof on the monitor 104b, and transmits the determination result via the determination result feeding device 132 to the navigation device body 126B.

Based on the determination result thus transmitted, the navigation device body 126B assigns benign markers 192a and malignant markers 192b as the case may be to all the spots which have been observed via the beam scanning probe 102, and superimposes those markers on the navigation image 190, and transmits the resulting image information to the overlay monitor of the surgery microscope 152B for display.

Because the relative positions between benign markers 192a, malignant markers 192b and the pointer 191 on the navigation image are determined by calculation by the navigation device body 126B, the positions of the markers, for example, relative to the pointer will be maintained even if the optical visual area 182 of the surgery microscope 152B is moved. The navigation image 190 is then superimposed on an optical image of the surgery microscope 152B on the overlay monitor, to give an optical visual area 182 as shown in FIG. 21.

Based on the distribution of the benign markers 192a and the malignant markers 192b, the navigation device body 126B determines the extent of malignant parts, and superimposes the malignant expansion 193 thus determined over the navigation image 190, and transmits the resulting image information to the overlay monitor. There the image is displayed on the optical visual area 182 of the surgery microscope 152B.

Consequently, the fifth embodiment, in addition to the advantages as obtained from the third embodiment, allows the operator to study a lesion without diverting his eyes from a microscope, and to check what fraction of the lesion is left intact on a real time basis.

Moreover, the previously described U.S. Pat. No. 6,006,126 discloses the known technology of establishing the correlation among an observational position of an optical microscope, a probe, and a navigation image (CT/MRI), in the three-dimensional space. Also, the U.S. Pat. No. 6,081,336 discloses the technology to establish the correlation between a microscope and a therapeutic equipment in the three-dimensional space. The disclosure of the U.S. Pat. No. 6,081,336 is incorporated in present invention by reference. When these technologies in the U.S. Pat. Nos. 6,006,126 and 6,081,336 are applied in the embodiments disclosed in present invention, it becomes possible for the surgeon to establish the correlation among an optical visual area image, cytological picture, beam scanning probe, navigation image and pathological diagnostic results and the like, in the three-dimensional space. It also becomes possible to superimpose and display information necessary for the monitoring.

It is obvious that widely different embodiments can be designed by referring to this invention without departing from the spirit and scope of this invention. Thus, the scope of this invention should not be limited by any particular embodiments except by the attended claims.

What is claimed is:

1. A beam scanning probe system for surgery comprising:
   image acquiring means for acquiring an image of a lesion to be operated on in the head;
   a laser beam scanning probe for acquiring optical image information, including a cytological picture, of a specific site of the lesion by confocally scanning light reflected by the specific site;
   a detection means for detecting the position of an observation point of the laser beam scanning probe relative to the site of the lesion;
   a recording means for recording, in a paired fashion, two image information: one relating to the cytological picture obtained via the beam scanning probe, and the other to an image of the lesion upon which the information regarding the position of the observation point of the beam scanning probe is superimposed;
   a transmitting means for transmitting image information and observation point information of the beam scanning probe, determination information of the cytological picture, and instruction information introduced based on the determination information of the cytological picture;
   a terminal for transmitting/receiving information transmitted by the transmitting means;
   a determination result feeding means for feeding a determination result of the cytological picture;
   a determination result displaying means for displaying at least two kinds of determination based on determination results provided by the determination result feeding means; and
   a superimposing means for superimposing the determination results provided by the determination result displaying means on the image of the lesion, based on the observation point position of the beam scanning probe relative to the site of the lesion.

2. A beam scanning probe system for surgery according to claim 1, further comprising:
   a computation means for determining a specific area based on determination results provided by the determination result displaying means; and
   a specific area displaying means for displaying the specific area determined by the computation means, wherein: the superimposing means superimposes at least one chosen from the specific area to be displayed and the determination results to be displayed, upon an image of a lesion to be operated on.

3. A beam scanning probe system for surgery according to claim 2, wherein: the computation means takes two marker points having different determination results, determines a point between the two according to a predetermined ratio, connect the mid-points thus determined to obtain a closed outline, and takes the area surrounded by the outline as the specific area.

4. A beam scanning probe system for surgery according to claim 1, wherein: the recording means stores the determination results to be displayed provided by the determination result displaying means in connection with cytological pictures, comprising:
   an input selection means for selectively feeding input from among the determination results to be displayed; and a read means for reading an appropriate cytological picture from the recording means based on the information selectively fed by the input selection means.

5. A beam scanning probe system for surgery comprising:
image acquiring means for acquiring image information including a lesion to be operated on of a test organ;
a monitor for displaying an image including the lesion based on the image information including the lesion;
a laser beam scanning probe for acquiring histological image information, including a cytological picture, from a specific site of the lesion by confocally scanning light reflected by the specific site;
a rigid sheath, including a hollow cavity through which the beam scanning probe is inserted down to its tip, the rigid sheath being able to guide the beam scanning probe inserted to its tip to the specific site;
a marker provided on the rigid sheath, the marker being apart by a predetermined distance from the tip of the rigid sheath;
a detector for detecting position information of the marker in a three-dimensional space;
a superimposed image generating circuit which obtains position information of the beam scanning probe in the three-dimensional space based on the position information of the marker, correlates the position information of the beam scanning probe with the image information of the lesion in the three-dimensional space, and obtains a superimposed image information where the position information of the beam scanning probe is superimposed upon the image information including the lesion; and
a memory for registering the superimposed image information and the histological image information correlated with the position information of the beam scanning probe, and registering the information as such.

6. A beam scanning probe system for surgery according to claim 1, wherein: the rigid sheath comprises a handle portion, a bend continuous with the handle portion, and a tip which is formed in the same direction with the extension of the bend extended in parallel with the extension of the handle portion.

* * * * *